US012357706B2

(12) United States Patent
Cao et al.

(10) Patent No.: US 12,357,706 B2
(45) Date of Patent: Jul. 15, 2025

(54) OPTIMIZED CYP4V2 GENE AND APPLICATION THEREOF

(71) Applicant: SUZHOU NGGT BIOTECHNOLOGY CO., LTD., Suzhou (CN)

(72) Inventors: Qing Cao, Suzhou (CN); Hai Zhang, Suzhou (CN); Shengmei Wen, Suzhou (CN); Lixin Jiang, Suzhou (CN)

(73) Assignee: SUZHOU NGGT BIOTECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 18/751,145

(22) Filed: Jun. 21, 2024

(65) Prior Publication Data

US 2024/0366794 A1 Nov. 7, 2024

Related U.S. Application Data

(63) Continuation of application No. PCT/CN2022/140586, filed on Dec. 21, 2022.

(30) Foreign Application Priority Data

Dec. 22, 2021 (CN) ........................ 202111580873.0

(51) Int. Cl.

| | |
|---|---|
| ***A61K 31/70*** | (2006.01) |
| ***A61K 48/00*** | (2006.01) |
| ***A61P 27/02*** | (2006.01) |
| ***C12N 9/02*** | (2006.01) |
| ***C12N 15/00*** | (2006.01) |
| ***C12N 15/63*** | (2006.01) |
| ***C12N 15/86*** | (2006.01) |
| *A01K 67/00* | (2006.01) |
| *A61K 38/00* | (2006.01) |

(52) U.S. Cl.

CPC ............ *A61K 48/005* (2013.01); *A61P 27/02* (2018.01); *C12N 9/0071* (2013.01); *C12N 15/86* (2013.01); *A61K 38/00* (2013.01); *C12N 2740/15043* (2013.01); *C12N 2740/16043* (2013.01); *C12N 2750/14143* (2013.01); *C12N 2770/32044* (2013.01); *C12N 2820/60* (2013.01); *C12N 2830/003* (2013.01); *C12N 2830/48* (2013.01); *C12N 2830/50* (2013.01); *C12Y 114/14001* (2013.01)

(58) Field of Classification Search

CPC ....... A61K 48/005; A61P 27/02; C12N 15/86; C12N 2740/15043

See application file for complete search history.

(56) References Cited

U.S. PATENT DOCUMENTS

| | | | | |
|---|---|---|---|---|
| 2020/0255859 | A1 | 8/2020 | Yang et al. | |
| 2022/0154211 | A1* | 5/2022 | Bell .................. | A61K 48/0058 |

FOREIGN PATENT DOCUMENTS

| | | | |
|---|---|---|---|
| CN | 111630170 | A | 9/2020 |
| CN | 113474461 | A | 10/2021 |
| CN | 113677801 | A | 11/2021 |
| CN | 114381465 | A | 4/2022 |
| WO | 2020117898 | A1 | 6/2020 |
| WO | 2020174368 | A1 | 9/2020 |
| WO | 2020174369 | A2 | 9/2020 |

OTHER PUBLICATIONS

Arguello-Astorga et al. Evolution of light-regulated plant promoters. Annu. Rev. Plant Physiol. Plant Mol. Biol. 49:525-555, (Year: 1998).*

Baruah et al. Dissecting the role of promoters of pathogen-sensitive genes in plant defense. Current Genomics 21:491-503, (Year: 2020).*

International Search Report dated Mar. 12, 2023, PCT Patent Application No. PCT/CN2022/140586, filed.

Ahmed, "Sustained Correction of a Murine Model of Phenylketonuria following a Single Intravenous Administration of AAVHSC15-PAH," Mol Ther Methods Clin Dev. Mar. 13, 2020; 17:568-580. doi: 10.1016/j.omtm.2020.03.009.

Clark, "Highly purified recombinant adeno-associated virus vectors are biologically active and free of detectable helper and wild-type viruses," Hum Gene Ther. Apr. 10, 1999; 10(6):1031-9. doi: 10.1089/10430349950018427.

Fisher, "Transduction with recombinant adeno-associated virus for gene therapy is limited by leading-strand synthesis," J Virol. Jan. 1996; 70(1): 520-532. doi: 10.1128/jvi.70.1.520-532.1996.

Garcia-Garcia, "Current perspectives in Bietti crystalline dystrophy," Clinical Ophthalmology, Jul. 30, 2019; 13:1379-1399. doi: 10.2147/OPTH.S185744.

Hata, "Reduction of lipid accumulation rescues Bietti's crystalline dystrophy phenotypes," Proceedings of the National Academy of Sciences, Mar. 26, 2018, 115 (15) 3936-3941, https://doi.org/10.1073/pnas.1717338115.

Jarrar, "Molecular Functionality of Cytochrome P450 4 (CYP4) Genetic Polymorphisms and Their Clinical Implications," Int J Mol Sci. Aug. 31, 2019; 20(17):4274. doi: 10.3390/ijms20174274.

(Continued)

*Primary Examiner* — Quang Nguyen

(74) *Attorney, Agent, or Firm* — Squire Patton Boggs (US) LLP

(57) ABSTRACT

Provided are an optimized CPY4V2 gene and an application thereof. The gene relates to a polynucleotide for coding a CYP4V2 protein, and comprises a nucleotide sequence having 90% or over 90% of identity with a nucleotide sequence as shown in SEQ ID NO: 5, SEQ ID NO: 6, SEQ ID NO: 7, SEQ ID NO: 8 or SEQ ID NO: 9. Also provided is an expression vector comprising the gene. The expression vector can realize lasting and stable expression in retinal pigment epithelium of eyes, can effectively reduce the dosage and possible side effects of a gene therapy drug for treating BCD, and improves the therapeutic effect.

64 Claims, 4 Drawing Sheets

Specification includes a Sequence Listing.

(56) References Cited

OTHER PUBLICATIONS

Jia, "Generation and characterization of Cyp4v3 gene knockout mice," Beijing Da Xue Xue Bao Yi Xue Ban. Dec. 18, 2021;53(6):1099-1106. Chinese. doi: 10.19723/j.issn.1671-167X.2021.06.016.

Ke, et al., "Clinical features of Bietti crystalline corneoretinal dystrophy caused by mutations in the CYP4V2 gene[J]," Ophthalmology in China, doi: 10.13281/j.cnki.issn.1004-4469.2020.02.005.

Konkle, "BAX 335 hemophilia B gene therapy clinical trial results: potential impact of CpG sequences on gene expression," Blood. Feb. 11, 2021; 137(6):763-774. doi: 10.1182/blood.2019004625.

Lai, "Alterations in serum fatty acid concentrations and desaturase activities in Bietti crystalline dystrophy unaffected by CYP4V2 genotypes," Invest Ophthalmol Vis Sci. Feb. 2010; 51(2):1092-7. doi: 10.1167/iovs.09-3665. Epub Sep. 24, 2009.

Li, Bietti crystalline corneoretinal dystrophy is caused by mutations in the novel gene CYP4V2. Am J Hum Genet., May 2004; 74(5):817-26. doi: 10.1086/383228. Epub Mar. 23, 2004.

Lockhart, "Generation and characterization of a murine model of Bietti crystalline dystrophy," Invest Ophthalmol Vis Sci. Aug. 12, 2014; 55(9):5572-81. doi: 10.1167/iovs.13-13717.

Mauro, "Codon Optimization in the Production of Recombinant Biotherapeutics: Potential Risks and Considerations," BioDrugs. Feb. 2018; 32(1):69-81. doi: 10.1007/s40259-018-0261-x.

McCarty, "Self-complementary AAV vectors; advances and applications," Mol Ther. Oct. 2008; 16(10):1648-56. doi: 10.1038/mt.2008.171.

McLaughlin, "Adeno-associated virus general transduction vectors: analysis of proviral structures," J Virol. Jun. 1988; 62(6): 1963-1973. doi: 10.1128/jvi.62.6.1963-1973.1988.

Ng, "Genetics of Bietti Crystalline Dystrophy," Asia Pac J Ophthalmol (Phila). Jul.-Aug. 2016; 5(4):245-52. doi: 10.1097/APO.0000000000000209.

Qu, "Treating Bietti crystalline dystrophy in a high-fat diet-exacerbated murine model using gene therapy," Gene Ther. Aug. 2020; 27(7-8):370-382. doi: 10.1038/s41434-020-0159-3.

Veldwijk, "Development and optimization of a real-time quantitative PCR-based method for the titration of AAV-2 vector stocks," Molecular Therapy, Aug. 2002; 6(2):272-8. doi: 10.1006/mthe.2002.0659.

Von Drygalski, "Etranacogene dezaparvovec (AMT-061 phase 2b): normal/near normal FIX activity and bleed cessation in hemophilia B," Blood Adv. Nov. 12, 2019; 3(21):3241-3247. doi: 10.1182/bloodadvances.2019000811.

Wang, "New compound heterozygous CYP4V2 mutations in bietti crystalline corneoretinal dystrophy," Gene. Jul. 20, 2021; 790:145698. doi: 10.1016/j.gene.2021.145698. Epub May 5, 2021.

Wang, "Validation of in vitro gene therapy for Bietti crystalline dystrophy," ARVO Annual Meeting Abstract, Jul. 2019, Investigative Ophthalmology & Visual Science Jul. 2019, vol. 60, 3420.

Xiao, "Gene transfer by adeno-associated virus vectors into the central nervous system," Exp Neurol. Mar. 1997; 144(1):113-24. doi: 10.1006/exnr.1996.6396.

Zhang, "PSCs Reveal PUFA-Provoked Mitochondrial Stress as a Central Node Potentiating RPE Degeneration in Bietti's Crystalline Dystrophy," Mol Ther. Dec. 2, 2020; 28(12):2642-2661. doi: 10.1016/j.ymthe.2020.07.024. Epub Jul. 25, 2020.

First Office Opinion Notice, dated Feb. 17, 2023, Chinese Application No. 20211580873.0.

Yang, et al., India Patent Application No. IN202017008657A, entitled "Cellular Models of and Therapies for Ocular Diseases," Applicant: Reflection Biotechnologies Limited, filed Feb. 28, 2020.

* cited by examiner

OPTIMIZED CYP4V2 GENE AND APPLICATION THEREOF

CROSS-REFERENCE TO RELATED APPLICATIONS

This application is a continuation of International Application No. PCT/CN2022/140586, filed on Dec. 21, 2022, which claims the benefit of Chinese Patent Application No. 20111580873.0, filed on Dec. 22, 2021, each of which is incorporated by reference herein in its entirety.

REFERENCE TO AN ELECTRONIC SEQUENCE LISTING

The contents of the electronic sequence listing (MTP21296_US_v2.xml; Size: 59,554 bytes; and Date of Creation Jan. 6, 2025) are herein incorporated by reference in their entireties.

TECHNICAL FIELD

The present disclosure is in the field of gene therapy and specifically relates to optimized CYP4V2 gene expression for gene therapy against Bietti crystalline dystrophy (BCD).

BACKGROUND ART

Bietti crystalline dystrophy (BCD, human Mendelian genetic disease OMIM210370) is a rare hereditary autosomal recessive disease with a biallelic mutation in the CYP4V2 gene. The disease was first described in 1937 by Italian doctor G. B. Bietti. It is characterized by the presence of numerous fine, shiny, yellow-white, crystalline-like deposits at the posterior pole of the retina, atrophy of the retinal pigment epithelium (RPE), pigment clots, and choroidal sclerosis. Progression of the disease ultimately results in decreased vision, night blindness, visual field loss, and impaired color vision. The onset of the disease may occur from adolescence to the age of thirty, but may also occur after the age of thirty. As the disease progresses, loss of peripheral vision, central vision, or both ultimately lead to legal blindness in most patients (Garcia-Garcia, Martinez-Rubio, et al. (2019). "Current perspectives in Bietti crystalline dystrophy." Clin Ophthalmol 13: 1379-1399).

BCD is caused by a mutation in the CYP4V2 gene. This gene is located on the long arm of human chromosome 4 and encodes an important 525 amino acid protein member of cytochrome P450 (family 4, subfamily IV, peptide 2), which is involved in fatty acid metabolism (Li, Jiao et al. (2004). "Bietti crystalline corneoretinal dystrophy is caused by mutations in the novel gene CYP4V2." Am J Hum Genet 74(5): 817-826). The CYP4V2 protein is present in the epithelial cells of the retina and cornea and the enzyme is localized to the endoplasmic reticulum. This enzyme has the typical omega-hydroxylase activity of CYP4 for medium-chain saturated fatty acids. CYP4V2 is the only CYP4 present at a significant level in retinal cells, and it may be an important contributor to the metabolism of polyunsaturated fatty acids in retinal cells. Gene mutations leading to defective catalytic function of CYP4V2 block degradation of ocular lipids and subsequent accumulation in the eyes of BCD patients (Hata, Ikeda, et al. (2018). "Reduction of lipid accumulation rescues Bietti's crystalline dystrophy phenotypes." Proc Natl Acad Sci USA 115(15): 3936-3941; Zhang, Yan, et al. (2020). "PSCs Reveal PUFA-Provoked Mitochondrial Stress as a Central Node Potentiating RPE Degeneration in Bietti's Crystalline Dystrophy." Mol Ther 28(12): 2642-2661). Systemic lipid inclusion was also found in some patients (Lai, Chu, et al. (2010). "Alterations in serum fatty acid concentrations and desaturase activities in Bietti crystalline dystrophy unaffected by CYP4V2 genotypes." Invest Ophthalmol Vis Sci 51(2): 1092-1097).

It is estimated that one out of every 67,000 people experiences BCD. It is more common in populations of East Asian descent, especially in Chinese and Japanese backgrounds. It is estimated that there are 21,000 patients in China and approximately 5,000 patients in the United States. BCD may be undiagnosed because its symptoms resemble those of other ocular diseases that gradually damage the retina. Currently, there is no treatment available for BCD (Ng, Lai, et al. (2016). "Genetics of Bietti Crystalline Dystrophy." Asia Pac J Ophthalmol (Phila) 5(4): 245-252; Wang, Chen, et al. (2021). "New compound heterozygous CYP4V2 mutations in bietti crystalline corneoretinal dystrophy." Gene 790: 145698).

BCD's gene therapy strategy is under development. In an HFD-induced BCD mouse model, the human CYP4V2 gene carried by an AAV vector is expressed in the RPE layer by subretinal injection, effectively restoring some physiological and functional defects, conceptually validating gene therapy for BCD disease (Qu, Wu et al. (2020). "Treating Bietti crystalline dystrophy in a high-fat diet-exacerbated murine model using gene therapy." Gene Ther 27(7-8): 370-382). Currently, AAV-mediated CYP4V2 gene therapy is at an early stage of research and development in several pharmaceutical companies. To date, there have been no reports proving that CYP4V2 can be fully and continuously expressed in vivo to achieve effective therapeutic effects.

SUMMARY OF THE INVENTION

To solve the problems existing in the prior art, it is an object of the present disclosure to provide a viral vector for optimizing gene expression to efficiently and persistently, and stably express human CYP4V2 in the retinal RPE layer of the eye and for treating BCD.

In one aspect, the present disclosure provides a polynucleotide encoding a CYP4V2 protein comprising a nucleotide sequence having 90% or more, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 5, SEQ ID NO: 6, SEQ ID NO: 7, SEQ ID NO: 8 or SEQ ID NO: 9.

In some embodiments of the disclosure, the polynucleotide is shown in SEQ ID NO: 5, SEQ ID NO: 6, SEQ ID NO: 7, SEQ ID NO: 8, or SEQ ID NO: 9.

In some embodiments of the disclosure, the polynucleotide is shown in SEQ ID NO: 5.

In another aspect, the present disclosure provides an expression cassette comprising the polynucleotide and a promoter operably linked to the polynucleotide.

In the other hand, the present disclosure provides a vector comprising polynucleotides of the aforementioned aspects, comprising the polynucleotides or the expression cassette.

In some embodiments of the present disclosure, the polynucleotide encoding the CYP4V2 protein is operably connected to an expression control element.

In some embodiments of the present disclosure, the expression control element is selected from one or more of a transcription/translation control signal, an origin of replication, a promoter, an enhancer, an intron, a polyA signal, ITR, an insulator, an RNA processing signal, and an element enhancing the stability of mRNA and/or proteins.

In another aspect, the disclosure provides a cell containing the expression vector.

In another aspect, the disclosure provides a viral particle comprising the expression vector.

In another aspect, the present disclosure provides a pharmaceutical composition for treating BCD comprising the polynucleotide, the expression cassette, the expression vector and/or the viral particle, and a pharmaceutically acceptable carrier, wherein the pharmaceutical composition expresses wild-type or codon-optimized CYP4V2 protein.

In another aspect, the present disclosure provides the use of the polynucleotide, the expression cassette, the expression vector, the viral particle, and/or the pharmaceutical composition for the manufacture of a medicament for the treatment of Bietti crystalline dystrophy (BCD).

In another aspect, the present disclosure provides a method for treating BCD, the method comprising administering to a subject an effective amount of the polynucleotide, the expression cassette, the expression vector, the viral particle, and/or the pharmaceutical composition.

In another aspect, the present disclosure provides a method of constructing a BCD cell model with a CYP4V2 mutation comprising the steps:

(1) designing sgRNA against CYP4V2 gene;

(2) constructing the sgRNA obtained in step (1) into a Cas9-sgRNA vector to obtain a Cas9-sgRNA plasmid; and (3) introducing the Cas9-sgRNA plasmid obtained in step (2) into a cell to obtain a cell having a CYP4V2 gene mutation.

BRIEF DESCRIPTION OF THE DRAWINGS

FIG. 4 shows the establishment and phenotypic characterization of the HEK293 CYP4V2 mutant cell model. CYP4V2 mutated HEK293 cells exhibit a defective cellular phenotype. Among them, (A) a schematic diagram of the exon 5 mutation of CYP4V2 was generated using CRIPSR/Cas9 method. The nucleotide sequence at the top of FIG. 4A is a fragment between 5964 bp and 6060 bp of the genome sequence of the wild-type human CYP4V2 gene (GeneID: 285440, RefSeqGene ID: NG_007965.1). The sense and anti-sense strands of the DNA sequence, and the amino acid sequence shown in the figure are set forth in SEQ ID NOS: 29, 30, and 31, respectively. (B) Sanger sequencing result of CYP4V2 gene targeting site in HEK293 exon 5 mutant cell clone 14 (5-C14). The nucleotide sequence of Exon5-sgRNA shown in the figure is set forth in SEQ ID NO: 18. (C) Evaluation of the cell proliferation rate of HEK293 WT and mutant 5-C14 cells during 6 days of culture (compared to WT: , $p<0.01$; *, $p<0.005$; student test; n=4). (D-E) Evaluation of the autophagy marker LC3B-I/II in HEK293 WT and mutant cells in the presence or absence of treatment with bafilomycin-A1 (Baf, 100 nM, 2 h). (D) Representative images of Western blot. (E) Quantification of LC3B-II protein levels, normalized to GAPDH and calculated as a ratio to WT cells without Baf treatment (NT) (*, $p<0.05$; ns: no significant difference; student test; n=3).

FIG. 5 shows the establishment of a CYP4V2 mutant ARPE-19 cell model, phenotypic characterization, and the effect of AAV2-CYP4V2 WT and the optimized gene opt18 on the phenotype of the ARPE-19 mutant cell model. The CYP4V2 exon 5 mutation was generated using the CRISPR/Cas9 method. Among them, (A) sanger sequencing of CYP4V2 gene targeting site in ARPE-19 cells. The nucleotide sequence of Exon5-sgRNA shown in the figure is set forth in SEQ ID NO: 18. (B) The cell proliferation rate of WT and mutant 5-C13 cells was assessed during a 6-day culture period. *, $P<0.01$; student test; n=6. (C) Cellular lipid deposition. 5-C13 cells were infected by WT, mutant 5-C13 cells, AAV2-CYP4V2 WT or opt18 with MOI 20000. Lipids and DAPI staining of cells after arachidonic acid (AA) treatment. Representative image of a laser confocal microscope. Scale bar, 25 microns. (D) Quantification of intracellular fat particle deposition. After infecting mutant cells with AAV2 CYP4V WT and opt18, the deposition of fat particles was significantly reduced. The effect of opt18 on the reduction of fat particle deposition was superior to WT (*, $p<0.005$; ****, $p<0.001$; n=50, student test). (E) Electron micrograph of WT and mutant cell 5-C13 showing autophagic vacuoles (black arrows) and vacuoles (white arrows). Scale bar, 500 nm.

FIG. 6 shows the effect of AAV2-CYP4V2 WT and an optimized gene on the phenotype of a HEK293 CYP4V2 mutant cell model. (A) Western blot detection of CYP4V2 protein expression levels in AAV2 CYP4V2 WT or opt18 or EGFP control cells after 2 days of MOI 20000 infection. (B) Evaluation of the cell proliferation rate during a 6-day period after infection. (C) On day 6, cell proliferation in HEK293 mutant cells infected with MOI 5000 or 20000 using AAV2 CYP4V2 opt18 or an EGFP control. (D) On day 6, cell proliferation comparison between wild-type HEK293 cells and HEK293 mutant cells infected with AAV2-CYP4V2 opt18 and EGFP control with MOI 20000 (*, $p<0.05$; ****, $p<0.001$; N=6, student test). (E-F) Evaluation of the autophagy marker LC3B-I/II in HEK293 mutant cells infected with AAV2-CYP4V2 WT opt18 and EGFP control with MOI 20000 with or without Baf treatment. (E) Representative images of Western blots. (F) Quantification of LC3B-II protein levels normalized to GAPDH and calculated as a ratio of EGFP NT conditions (*, $p<0.05$; **, $p<0.01$; ns: no significant difference; student test; n=3).

DETAILED DESCRIPTION OF THE INVENTION

Figure 1:
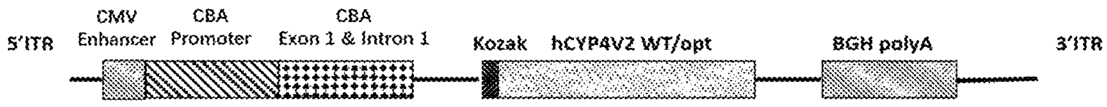
FIG. 1 is a schematic diagram of the structure of a CYP4V2 expression cassette of a recombinant AAV (rAAV) vector disclosed in this disclosure.

In this disclosure, unless otherwise stated, the scientific and technical terms used herein have the meanings commonly understood by those skilled in the art. Also, as used herein, protein and nucleic acid chemistry, molecular biology, cell and tissue culture, microbiology, immunology, and laboratory procedures used herein are terms and routine procedures widely used in the corresponding fields. Meanwhile, in order to better understand the present disclosure, definitions and explanations of related terms are provided below.

As mentioned in this article, "about" a certain value or parameter includes (and describes) implementation solutions for the value or parameter itself. For example, a description referring to "about X" includes a description of "X".

As used herein, the singular forms "a", "an", and "the" include plural referents unless the context clearly dictates otherwise.

A "vector" as used herein refers to a recombinant plasmid or virus comprising a nucleic acid to be delivered into a host cell (in vitro or in vivo).

The term "polynucleotide" or "nucleic acid" as used herein refers to a polymeric form of nucleotides of any length, either a ribonucleotide or a deoxyribonucleotide. Thus, the term includes, but is not limited to, single, double or multi-stranded DNA or RNA, genomic DNA, cDNA, DNA-RNA hybrids or polymers comprising purine and pyrimidine bases or other natural, chemically or biochemically modified, non-natural or derivatized nucleotide bases. The backbone of the nucleic acid may comprise sugar and phosphate groups (as commonly found in RNA or DNA), or modified or substituted sugar or phosphate groups. Alternatively, the backbone of the nucleic acid may comprise a polymer of synthetic subunits such as phosphoramidates and thus may be oligodeoxynucleoside phosphoramidates ($P—NH_2$) or mixed phosphoramidate-phosphodiester oligomers. In addition, double-stranded nucleic acids can be obtained from single-stranded polynucleotide products that are chemically synthesized (either by synthesizing the complementary strand under appropriate conditions and annealing the strand, or by synthesizing the complementary strand de novo using DNA polymerase with appropriate primers).

A "recombinant viral vector" refers to a recombinant polynucleotide vector comprising one or more heterologous sequences (i.e. nucleic acid sequences of non-viral origin). In the case of recombinant AAV vectors, the recombinant nucleic acid is flanked by at least one, preferably two inverted terminal repeats (ITR).

A "recombinant AAV vector (rAAV vector)" refers to a polynucleotide vector comprising one or more heterologous sequences (i.e. non-AAV derived nucleic acid sequences) flanked by at least one, and preferably two, AAV inverted terminal repeats (ITR). When present in a host cell that has been infected with an appropriate helper virus (or expresses an appropriate helper function) and expresses the AAV rep and cap gene products (i.e. AAV Rep and Cap proteins), the rAAV vector can replicate and package into infected viral particles. When the rAAV vector is incorporated into a larger polynucleotide (e.g. in a chromosome or another vector such as a plasmid for cloning or transfection), the rAAV vector may be referred to as a "pro-vector" which can be "rescued" by replication and encapsidation in the presence of the AAV packaging function and appropriate helper functions. The rAAV vector can be any of a variety of forms, including but not limited to a plasmid, a linear artificial chromosome, which can be complexed with a liposome, encapsulated within a liposome, and in embodiments, encapsulated in a viral particle, particularly an AAV particle. rAAV vectors can be packaged into an AAV viral capsid to produce "recombinant adeno-associated virus particles (rAAV particles)". AAV helper functions (i.e. functions that allow AAV replication and packaging from a host cell) can be provided in any of a variety of forms, including, but not limited to, helper viruses or helper viral genes that facilitate AAV replication and packaging. Other AAV helper functions are known in the art.

"rAAV virus" or "rAAV viral particle" refers to a viral particle consisting of at least one AAV capsid protein and an encapsidated rAAV vector genome.

"heterologous" means an entity that differs in genotype from the rest of the entity to which it is compared or into which it is introduced or incorporated. For example, nucleic acids introduced into different cell types by genetic engineering techniques are heterologous nucleic acids (and, when expressed, may encode heterologous polypeptides). Similarly, a cellular sequence (e.g. a gene or portion thereof) incorporated into a viral vector is a heterologous nucleotide sequence with respect to the vector.

As used in reference to viral titer, the term "genomic particle (gp)", "genomic equivalent" or "genomic copy" refers to the number of virions comprising the recombinant AAV DNA genome, whether infectious or functional. The number of genomic particles in a particular vector preparation can be determined by methods such as those described in the examples herein or, for example, by Clark et al. (1999) Hum. Gene Ther. 10: 1031-1039; Veldwijk et al. (2002) Mol. Ther. 6: 272-278.

As used in reference to viral titer, the term "infectious unit (iu)", "infectious particle" or "replication unit" refers to the number of recombinant AAV vector particles that have the ability to infect and replicate as measured by an infection center assay, also referred to as a replication center assay, as described, for example, in McLaughlin et al. (1988) J. Virol. 62: 1963-1973.

As used in reference to viral titer, the term "transduction unit (tu)" refers to the number of infectious recombinant AAV vector particles that result in the production of a functional transgene product, as measured in a functional assay, as exemplified herein or, for example, in Xiao et al.

(1997) Exp. Neurobiol., 144:113-124; or Fisher et al. (1996) J. Virol., 70:520-532 (LFU assay).

An "inverted terminal repeat" or "ITR" sequence is a term well-known in the art and refers to a relatively short sequence found at the end of the viral genome, in the opposite direction.

An "AAV inverted terminal repeat (ITR)" sequence is a well-known term in the art and is a sequence of about 145 nucleotides found at both ends of the native single-stranded AAV genome. The outermost 125 nucleotides of an ITR can exist in either of two alternative orientations, resulting in heterogeneity between different AAV genomes and between the two ends of a single AAV genome. The outermost 125 nucleotides also contain several shorter regions that are self-complementary (referred to as the A, A', B, B', C, C' and D regions), allowing interstrand base pairing to occur within the ITR portion.

A "helper virus" for AAV refers to a virus that allows AAV (which is a defective parvovirus) to replicate and package through a host cell. A variety of such helper viruses have been identified, including adenoviruses, herpes viruses, and poxviruses such as vaccinia. Adenoviruses encompass a number of different subtypes, although adenovirus type 5 (Ad5) of subtype C is most commonly used. A variety of adenoviruses of human, non-human mammalian, and avian origin are known and available from depositories such as ATCC. The herpes virus family, which is also available from depositories such as ATCC, includes for example herpes simplex virus (HSV), Epstein-Barr viruses (EBV), cytomegaloviruses (CMV), and pseudorabies viruses (PRV).

The "percentage (%) sequence identity" relative to the reference peptide or nucleic acid sequence is defined as the percentage of amino acid residues or nucleotides in the candidate sequence that are identical to the amino acid residues or nucleotides in the reference peptide or nucleic acid sequence after aligning the sequence and introducing gaps (if necessary, to achieve maximum percentage sequence identity without considering any conservative substitutions as part of sequence identity). Alignment for purposes of determining percent amino acid or nucleic acid sequence identity can be accomplished in a variety of ways in the art, for example, using publicly available computer software programs, such as those described in Current Protocols in Molecular Biology (Ausubel et al. eds. 1987), Supp. 30, section 7.7.18, Table 7.7.1, and including BLAST, BLAST-2, ALIGN, or the Megalign (DNASTAR) software. A preferred alignment software is ALIGN Plus (Scientific and Educational Software, Pennsylvania). Those skilled in the art can determine appropriate parameters for measuring alignment, including any algorithm that needs to achieve maximum alignment over the full length of the compared sequence. For purposes herein, the % amino acid sequence identity of a given amino acid sequence A to, with, or against a given amino acid sequence B (which may alternatively be referred to as amino acid sequence A having or comprising a certain % amino acid sequence identity to, with or against a given amino acid sequence B) is calculated as follows: 100 times the score X/Y, where X is the number of amino acid residues in the program alignment of A and B that are scored as identical matches by the sequence alignment program, and where Y is the total number of amino acid residues in B. It will be appreciated that where the length of amino acid sequence A is not equal to the length of amino acid sequence B, the % amino acid sequence identity of A to B will not be equal to the % amino acid sequence identity of B to A. For purposes herein, the % nucleic acid sequence identity of a given nucleic acid sequence C to, with, or against a given nucleic acid sequence D (which may alternatively be referred to as a given nucleic acid sequence C having a certain % nucleic acid sequence identity to, with or against a given nucleic acid sequence D) is calculated as follows: 100 times the score W/Z, where W is the number of nucleotides scored as identical matches by the sequence alignment program in the programmed alignment of C and D, and where Z is the total number of nucleotides in D. It will be appreciated that where the length of nucleic acid sequence C is not equal to the length of nucleic acid sequence D, the % nucleic acid sequence identity of C to D will not be equal to the % nucleic acid sequence identity of D to C.

The "effective amount" is the amount that is sufficient to affect beneficial or expected outcomes, including clinical outcomes (such as improving symptoms, achieving clinical endpoints, etc.). An effective amount can be administered once or multiple times. For disease states, an effective amount is an amount sufficient to ameliorate, stabilize, or delay disease progression. For example, an effective amount of rAAV particles expresses a desired amount of a heterologous nucleic acid such as a therapeutic polypeptide or therapeutic nucleic acid.

The "individual" or "subject" is a mammal. Mammals include but are not limited to, domesticated animals (e.g. cows, sheep, cats, dogs, and horses), primates (e.g. humans and non-human primates such as monkeys), rabbits, and rodents (e.g. mice and rats). In some embodiments, the individual or subject is a human.

"Treatment" as used herein is a means for obtaining beneficial or desired clinical results. For purposes of this disclosure, beneficial or expected clinical results include but are not limited to, amelioration of symptoms, diminishment of extent of disease, stabilization (such as non-worsening) of the disease, prevention of disease spread (such as metastasis), delay or alleviation of disease progression, improvement or alleviation of disease status, and remission (whether partial or total), whether detectable or undetectable. "Treatment" may also mean prolonging survival as compared to expected survival if not receiving treatment.

In one aspect, the present disclosure provides a polynucleotide encoding a CYP4V2 protein comprising a nucleotide sequence having 90% or more, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 5, SEQ ID NO: 6, SEQ ID NO: 7, SEQ ID NO: 8 or SEQ ID NO: 9.

In some embodiments of the disclosure, the polynucleotide is as shown in SEQ ID NO: 5, SEQ ID NO: 6, SEQ ID NO: 7, SEQ ID NO: 8, or SEQ ID NO: 9.

In another aspect, the present disclosure provides an expression cassette comprising the polynucleotide and a promoter operably linked to the polynucleotide.

In another aspect, the present disclosure provides an expression vector comprising the polynucleotide or the expression cassette.

In some embodiments of the present disclosure, the polynucleotide encoding the CYP4V2 protein is operably connected to an expression control element.

In some embodiments of the present disclosure, the expression control element is selected from one or more of a transcription/translation control signal, an origin of replication, a promoter, an enhancer, an intron, a polyA signal, ITR, an insulator, an RNA processing signal, and an element enhancing the stability of mRNA and/or proteins.

In some embodiments of the present disclosure, the expression vector comprises an origin of replication; preferably, the origin of replication sequence is selected from the group consisting of f1 bacteriophage ori, RK2 oriV, pUC ori, and pSC101 ori.

In some embodiments of the present disclosure, the expression vector further comprises a 5' ITR; preferably, the 5' ITR comprises a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 1; more preferably, the polynucleotide is as shown in SEQ ID NO: 1.

In some embodiments of the present disclosure, the expression vector further comprises a 3' ITR; preferably, the 3' ITR comprises a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 11; more preferably, the polynucleotide is as shown in SEQ ID NO: 11.

In some embodiments of the present disclosure, the expression vector further comprises an enhancer; preferably, the enhancer is a CMV enhancer; more preferably, the enhancer comprises a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 2; more preferably, the polynucleotide is as shown in SEQ ID NO: 2.

In some embodiments of the present disclosure, the expression vector further comprises a promoter. In some embodiments of the present disclosure, the promoter is a specific or non-specific promoter. In some embodiments of the present disclosure, the promoter is selected from a CBA promoter, CMV promoter, SV40 promoter, hPGK promoter, and TRE 3GS promoter. In some embodiments of the present disclosure, the promoter is a CBA promoter; preferably the CBA promoter comprises a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 3. In some embodiments of the disclosure, the polynucleotide is as shown in SEQ ID NO: 3. In some embodiments of the present disclosure, the promoter is an inducible promoter. Preferably, the inducible system comprises one or more of a tetracycline-regulated promoter, an alcohol-regulated promoter, a steroid-regulated promoter, a metal-regulated promoter, a pathogenicity-regulated promoter, a temperature/heat-inducible promoter, and a light-regulated promoter, an and IPTG inducible system. In some embodiments of the disclosure, the tetracycline-regulated promoter is selected from a Tet on promoter, a Tet off promoter, and a Tet Activator promoter. In some embodiments of the present disclosure, the alcohol-regulated promoter is selected from an alcohol dehydrogenase I (alcA) gene promoter, a promoter responsive to an alcohol transactivator protein (AlcR). In some embodiments of the present disclosure, the steroid-regulated promoter is selected from a rat glucocorticoid receptor promoter, a human estrogen receptor promoter, a moth ecdysone receptor promoter, a retinoid promoter, and a thyroid receptor superfamily promoter. In some embodiments of the present disclosure, the metal-regulated promoter is selected from yeast, mouse, and human metallothionein promoters. In some embodiments of the present disclosure, the pathogenic-regulated promoter is selected from a salicylic acid-regulated promoter, an ethylene-regulated promoter, and a benzothiadiazole-regulated (BTH) promoter. In some embodiments of the present disclosure, the temperature/heat-inducible promoter is selected from an HSP-70 promoter, an HSP-90 promoter, and a soybean heat shock promoter. In some embodiments of the present disclosure, the light regulatory promoter is a light-responsive promoter of plant cells.

In some embodiments of the present disclosure, the expression vector further comprises an exon and an intron. In some embodiments of the present disclosure, the exon and intron are the first exon and first intron of the chicken beta-actin gene. In some embodiments of the present disclosure, the exon and intron include a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 4. In some embodiments of the disclosure, the polynucleotide is as shown in SEQ ID NO: 4.

In some embodiments of the present disclosure, the expression vector further comprises a polyA signal. In some embodiments of the present disclosure, the polyA signal is bovine growth hormone poly A (BGH poly A), short poly A, SV40 polyA, and/or human beta-globin poly A. In some embodiments of the present disclosure, the polyA signal comprises a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 10. In some embodiments of the disclosure, the polynucleotide is as shown in SEQ ID NO: 10.

In some embodiments of the present disclosure, the expression vector comprises a nucleotide sequence having 90% or higher identity, preferably a nucleotide sequence having 91%, 92%, 93%, 94%, 95%, 96%, 97%, 98%, 99% or higher identity, more preferably a nucleotide sequence having 98%, 99%, or higher identity to the nucleotide sequence as shown in SEQ ID NO: 12, SEQ ID NO: 13, SEQ ID NO: 14, SEQ ID NO: 15, and SEQ ID NO: 16. In some embodiments of the disclosure, the polynucleotide is as shown in SEQ ID NO: 12, SEQ ID NO: 13, SEQ ID NO: 14, SEQ ID NO: 15 or SEQ ID NO: 16.

In some embodiments of the present disclosure, the vector comprises a post-transcriptional regulatory element. In some embodiments of the present disclosure, the post-transcriptional regulatory element is a woodchuck hepatitis virus post-transcriptional regulatory element (WPRE).

In some embodiments of the present disclosure, the vector further comprises a gene encoding a marker. In some embodiments of the present disclosure, the marker is selected from one or more of an antibiotic resistance protein, a toxin resistance protein, a colored or fluorescent or luminescent protein, and a protein mediating enhanced cell growth and/or gene amplification.

In some embodiments of the present disclosure, the antibiotic is selected from ampicillin, neomycin, G418, puromycin, and blasticidin.

In some embodiments of the present disclosure, the toxin is selected from anthrax toxin and diphtheria toxin.

In some embodiments of the present disclosure, the colored or fluorescent, or luminescent protein is selected from a green fluorescent protein, an enhanced green fluorescent protein, a red fluorescent protein, and luciferase. In some embodiments of the present disclosure, the protein mediating enhanced cell growth and/or gene amplification is dihydrofolate reductase (DHFR).

In some embodiments of the present disclosure, the expression vector is selected from a plasmid, cosmid, viral vector, RNA vector, or linear or circular DNA or RNA molecule.

In some embodiments disclosed herein, the plasmid is selected from pCI, puc57, pcDNA3, pSG5, pJ603, and pCMV In some embodiments of the present disclosure, the viral vector is selected from retrovirus, adenovirus, parvovirus (e.g. adeno-associated virus), coronavirus, negative-stranded RNA virus such as orthomyxovirus (e.g. influenza virus), rhabdovirus (e.g. rabies and vesicular stomatitis virus), paramyxovirus (e.g. measles and Sendai virus), positive-stranded RNA virus such as RNA parvoviruses and alphaviruses, and double-stranded DNA virus including adenoviruses, herpes virus (e.g. herpes simplex virus types 1 and 2, Epstein-Bar virus, cytomegalovirus) and poxviruses (e.g. cowpox virus, fowlpox virus, and canarypox virus), norwalk virus, togavirus, flavivirus, reovirus, papovavirus, hepadnavirus, baculovirus, and hepatitis virus.

In some embodiments of the present disclosure, the retrovirus is selected from avian leukosis-sarcoma, mammalian C-type, B-type viruses, D-type viruses, HTLV-BLV aggregate, lentivirus, and spumavirus.

In some embodiments of the present disclosure, the lentiviral vector is selected from HIV-1, HIV-2, SIV, FIV, BIV, EIAV, CAEV, and ovine demyelinating leukoencephalitis lentivirus.

In some embodiments of the present disclosure, the expression vector is an adeno-associated virus.

In some embodiments of the present disclosure, the adeno-associated virus is selected from AAV type 1, AAV type 2, AAV type 3, AAV type 4, AAV type 5, AAV type 6, AAV type 7, AAV type 8, AAV type 9, AAV type 10, avian AAV, bovine AAV, canine AAV, equine AAV, ovine AAV, and the like.

In some embodiments of the disclosure, the expression vector further comprises a shortened chimeric intron and a Kozak initiation sequence.

In some embodiments of the disclosure, the shortened chimeric intron is as shown in SEQ ID NO: 4.

In some embodiments of the present disclosure, the Kozak initiation sequence is as shown in SEQ ID NO: 17.

On the other hand, the present disclosure provides a viral particle comprising the expression vector.

In another aspect, the present disclosure provides a pharmaceutical composition for treating BCD comprising the polynucleotide, the expression cassette, any of the expression vectors and/or the viral particle, and a pharmaceutically acceptable carrier, wherein the pharmaceutical composition expresses wild-type or codon-optimized CYP4V2 protein.

In another aspect, the present disclosure provides the use of the polynucleotide, the expression cassette, the expression vector, the viral particle, and/or the pharmaceutical composition for the manufacture of a medicament for the treatment of Bietti crystalline dystrophy (BCD).

In another aspect, the present disclosure provides a method for treating BCD, the method comprising administering to a subject an effective amount of the polynucleotide, the expression cassette, the expression vector, the viral particle, and/or the pharmaceutical composition.

In another aspect, the present disclosure provides a method of constructing a BCD cell model with a CYP4V2 mutation comprising the steps:

(1) designing sgRNA against CYP4V2 gene;
(2) constructing the sgRNA obtained in step (1) into a Cas9-sgRNA vector to obtain a Cas9-sgRNA plasmid;
(3) introducing the Cas9-sgRNA plasmid obtained in step (3) into a cell to obtain a cell having a CYP4V2 gene mutation.

In some embodiments of the present disclosure, the method further comprises the step of (4) screening for cells having the CYP4V2 gene mutation.

In some embodiments of the present disclosure, the method further comprises the step of (5) identifying the CYP4V2 gene mutant cell.

In some embodiments of the present disclosure, the identification is selected from a cell proliferation assay, an autophagy change assay, and a fat particle deposition assay.

In some embodiments of the present disclosure, the sgRNA is selected from one or more of SEQ ID NOs: 18-21.

The present disclosure provides an adeno-associated viral vector expressing the codon-optimized CYP4V2 gene for efficient, sustained, and stable expression in the retinal pigment epithelial layer of the eye. The present disclosure can effectively reduce the dosage and possible side effects of gene therapy drugs for treating BCD, and improve the therapeutic effect.

For purposes of clarity and conciseness, features are described herein as part of the same or separate embodiments, however, it will be understood that the scope of the disclosure may include some embodiments having a combination of all or some of the features described.

The present disclosure is described in more detail below with reference to specific examples, which, however, are for illustrative purposes only and are not intended to limit the present disclosure.

Experimental Materials and Methods

CYP4V2 Expression Cassette and AAV Vector

All DNA sequences used in this study were synthesized by the Genscript. Codon optimization was improved using the GenSmart codon optimization tool. The AAV vector-mediated CYP4V2 expression cassette is shown in FIG. 1. The expression cassette sequence was cloned into a shuttle plasmid vector to obtain a shuttle plasmid containing the target gene CYP4V2 mediated by the AAV vector.

AAV Vector Production and Purification Method

The production of AAV vector uses a three-plasmid system, i.e. a shuttle plasmid containing the target gene CYP4V2, a pRepCap plasmid with the repcap gene of the AAV vector, and a helper plasmid pHelper, and uses PEI as a transfection reagent to co-transfect HEK293 cells and recombine to package an AAV virus vector. Harvesting was performed 48-72 hours after transfection, and the harvest solution was purified to obtain a recombinant AAV virus vector with a certain purity. The purification method was as follows:

The harvest fluid was first pretreated. The HEK293 cells were sufficiently lysed to release the intracellular AAV viral vector. The nuclease was added at the same time to digest the free nucleic acid. After digestion, the macromolecular impurities and cell debris were removed by deep filtration. The filtrate after deep filtration was subjected to secondary filtration to obtain a clear solution for affinity loading.

Affinity chromatography used the specific adsorption of a ligand and a protein to capture the AAV virus vector in the harvest solution, and removes most process-related impurities, achieving the effect of concentration and impurity removal. The collected eluate was mixed well and neutralized with a neutralization buffer and stored in a sterile stock solution bottle as an anion chromatography loading solution.

Anion chromatography used the isoelectric point difference of different components to separate solid and empty-shelled AAV viruses while continuing to remove the residual impurities. The eluent was collected in a new sterile liquid storage bottle. The buffer solution was replaced by the ultrafiltration concentration method to be the buffer solution with stable preparation, while the virus titer was concentrated to about $5\times10^{12}$ vg/mL. Finally, the solution was sterilized, filtered, and dispensed for future use.

Titer Quantification of AAV Vector Stocks

After AAV virus purification was complete, the amount of virus needed to be determined. The genomic titer is the most classical standard for characterizing the physical titer of AAV Designing primer probes against the genomic sequence of rAAV followed by Q-PCR detection is the most common method for genomic titer detection.

In view of the codon optimization of the ORF coding frame in the present disclosure, involving screening of multiple vector structures, the consensus sequences in the vectors are selected to design primer probes in order to ensure quantitative stability and accuracy between different vector structures. The CMV enhancer sequence is a portion of the CAG promoter that is common to different vector constructs during codon optimization, so primer probes are designed for this sequence.

In the process of genome titer detection, the standard curve shall be established first. The positive standard plasmid shall be diluted to $2\times10^7$, $2\times10^6$, $2\times10^5$, $2\times10^4$, $2\times10^3$, and $2\times10^2$ copies/μl using a sample diluent as a template of the standard curve. The linearity and amplification efficiency of the standard curve shall be controlled. Generally, R2>0.99, and the amplification efficiency shall be between 90%-110%. Then, the pretreated rAAV sample was diluted and then subjected to QPCR detection, so as to ensure that the Ct value detected by the sample is within the range of the standard curve. The genome titer of the rAAV sample was calculated by substituting the Ct value of the sample into the standard curve, and the content of the product was identified.

In Vitro Cell Plasmid Transfection Experiment

HEK293 cells were digested one day in advance and seeded into a 6-well plate at $7.0*10^5$ cells/well. The plasmid transfection experiment was performed after overnight incubation. The plasmid was mixed with the transfection reagent in the following amounts: To a 1.5 ml centrifuge tube, 125 μl of opti-MEM medium (Gibco, 31985-070), 2 μg of CYP4V2-opt/WT expression plasmid, 200 ng of CMV-EGFP plasmid and 5 μl of P3000 were add and mixed well to obtain a plasmid tube. To another 1.5 ml centrifuge tube, 125 μl of opti-MEM medium and 5 μl of Lipo 3000 (Thermo, L3000015) were added, mixed well, and then added into the plasmid tube. Standing incubation was performed for 15 min at room temperature. The mixed solution was slowly dropped into HEK293 cells of the 6-well plate, and continued to culture in a $CO_2$ constant temperature incubator for 48 h.

In Vitro Cell Virus Infection Experiment

ARPE-19 cells were digested one day in advance and seeded into a 6-well plate at $3.0*10^5$ cells/well. The AAV2 virus infection experiment was performed after overnight incubation for 24 h. One well of cells was counted after digestion. The number of required virus Vg was calculated according to the 20000 MOI infection parameter, and the required amount of virus was diluted to 1 ml with Opti-MEM medium. Then, the cell culture medium in the 6-well plate inoculated overnight was cleaned and 1 ml of diluted virus solution was added. The culture was continued in the $CO_2$ constant temperature incubator. After 4 h, the system was supplemented with 1 ml of DMEM complete medium (DMEM+10% FBS+1% dual antibody medium (Hyclone, SV30010)), and placed in the $CO_2$ constant temperature incubator for culture for 48 h.

Construction of BCD Cell Model with CYP4V2 Mutation

The CRISPR-Cas9 method was used to construct the BCD cell model with CYP4V2 mutation. The specific method was as follows: HEK293 or ARPE-19 cells were subjected to digestion treatment one day in advance and inoculated into a 6-well plate at $7.0*10^5$ cells/well. After 24 h, the plasmid transfection experiment was performed. The plasmid sample dilution was prepared: into a 1.5 ml centrifuge tube, 125 μl of opti-MEM medium, 2 μg of Cas9-sgRNA plasmid (addgene, #58766), and 5 μl of P3000 (Exon7-sgRNA1-HDR repair construction supplemented with 3 μg of CYP4V2-ssDNA) were added and mixed well. Lipo 3000 (Thermo, L3000015) dilution was prepared: into a 1.5 ml centrifuge tube, 125 μl of opti-MEM medium and 5 μl of Lipo 3000 were added, mixed well, and added into the plasmid sample dilution tube. After mixing well, incubation was performed for 15 min at room temperature. The mixed solution was slowly dropped into the cells to be transfected of the 6-well plate, gently shaken for mixing well, and placed in a $CO_2$ constant temperature incubator for culture. 48 H after transfection, fluorescence photography was taken to confirm the transfection efficiency. The cells in the 6-well plate were digested, and DMEM complete medium containing 5 μg/ml Puromycin was added for pressure culture, during which the medium was changed every day, and the medium was DMEM-Full medium containing 5 μg/ml puromycin. After 72 h of culture, the cell culture medium in the 6-well plate was discarded, and the DMEM medium without puromycin was added for culture. After 48 h of culture, the cells were digested and counted, and sorted 1 cell/well into a 96-well plate (containing 200 μl of DMEM+20% FBS+1% dual-antibody medium). After 2-3 weeks of culture, clonal plaques were observed to grow up and step-wisely expanded based on 96 well plate→24 well plate→6 well plate. After the cells in the 6-well plate were completely grown, partial cells were taken to extract the cell genome DNA (Tiangen, DP304-03), which was amplified by PCR. After gel cutting and recycling, Sanger sequencing was performed for validation. The genotype of monoclonal cells was analyzed using SeqMan software. The remaining cells were expanded and cryopreserved according to the needs of the experiment.

Western Blot Analysis

200 μl of RIPA lysis solution containing a protease inhibitor (Beyotime Biotechnology Co. Ltd. P0013 B) was added to each well of a 6-well plate seeded with cultured cells, and the cells were lysed thoroughly on ice for 5 min. The cell lysate was collected in a 1.5 ml centrifuge tube, and placed for 30 min on ice. After 20 min of centrifuge at 15000 g at 4° C., the supernatant was taken. The protein sample was diluted 10-fold with PBS and mixed well. Protein quantification was performed using the BCA protein quantification kit (Pierce™ BCA protein detection kit (Thermo Fisher, 23225). 5xSDS loading buffer was added to the protein sample and mixed well. 5 min of boiling was performed at 100° C. 30 μg protein sample was separated by SDS-PAGE electrophoresis and transferred to a PVDF membrane. After blocking with 5% skim milk (PBS) for 1 h at room temperature, the antibody was incubated and detected by ECL. Imaging analysis was performed by the Bio-Rad ChemiDoc™ Touch Imaging System.

Cell Proliferation Analysis

CYP4V2 mutated cells were digested with wild-type cells and counted. The cell suspension with adjusted cell density was mixed well and inoculated into a 96-well plate, with four duplicate wells for each cell. In in vitro efficacy experiments, virus infection was performed 24 h after seeding plates. The CCK-8 assay was performed 48 h after seeding and the days of the assay were day 2, day 3, day 4, day 5, and day 6. On the day of the assay, the number of total wells to be analyzed was counted and an appropriate amount of DMEM medium containing CCK-8 reagent was prepared. The amount of CCK-8 reagent (Dojindo Chemical Co. CK04) and DMEM medium was prepared in a ratio of 1:10. 100 μl of DMEM medium containing CCK-8 reagent was added to each well. After 1.5 h of incubation at 37° C. in a cell culture incubator, the plate was read at 450 nm using a multi-purpose microplate reader (BioTek, SYNERGY/LX). Statistical analysis of the data was performed using GraphPad Prism software.

Autophagosome Function Detection

Wild-type and mutant cells and virus-infected cells were treated with a culture medium containing 100 nM Bafilomycin-A1 (Baf) or without the drug for 2 h, respectively. Cell proteins were extracted, and the ratio of LC3B-II/GAPDH was analyzed by WB assay to determine whether intracellular autophagy was unobstructed.

Lipid Deposition Staining

Cells were treated with 160 μM arachidonic acid (AA) for 4 consecutive days and fixed with 4% paraformaldehyde at room temperature for 20 min. Cells were stained with 3 μM BODIPY 493/503 at 37° C. for 20 min. 10 Min of counterstaining was performed with 5 μg/ml DAPI. Photographs were taken with a laser confocal microscope. For each experimental group, 50 cells were selected, and the area of lipid deposition particles inside cells and the number of lipid deposition particles per unit area inside cells were analyzed using the Image pro plus software.

Subretinal Injection in Mice

Mydriasis was fully dilated after general anesthesia in mice. The sclera was punctured with a 30½ gauge disposable sharp needle outside the limbus of the corneosclera under direct vision of a special ophthalmological operating microscope to avoid injury to the iris and lens. Then a micro loader with a 33-gauge flat needle was introduced along the puncture site. The needle bypassed the lens and reached the vitreous body, and then gradually inserted into the potential retinal compartment between the neuroretinal layer and the retinal pigment epithelium (RPE) layer and slowly injected, wherein the injection volume was 1 μl of 0.1% Fluorescein sodium dye (safe concentration) was added into the injection vehicle suspension, so as to make it convenient to observe the success of the injection and the scope of retinal detachment. During the injection, 2.5% hydroxypropyl methylcellulose was dropped on the ocular surface to facilitate observation of the fundus at any time. The injection was successful as evidenced by a clear round bulge of the retina in the fundus and green color beneath the bulge under the operating microscope. After a certain time, the bleb disappeared, and the local retinal bulge became flat. Intraoperatively, if the clear round bulge of the retina in the fundus and green color beneath the bulge cannot be seen or if complications such as massive retinal hemorrhage can be seen, the mice will be re-injected. 1% Atropine eye ointment and tetracycline cortisone eye ointment were applied at the end of surgery and repeated every other day for three times to reduce inflammatory reaction and prevent infection.

Extracting Mouse Eyeball Retina Sample

Mouse eye tissues were taken, cornea and lens were removed. 100 μl of ATL solution (QIAGEN, 19076) was added to homogenize for 2 min. DNA Sample Extraction: 10 μl of the homogenate was aspirated; 10 μl of ATL solution and 2 μl of proteinase K (QIAGEN, 19133) were added to mix well; 20 μl of AL solution (QIAGEN, 19075) was added to mix well; incubation was performed at 56° C. for 10 min to prepare the DNA detection sample. Protein extraction: the remaining 50 μl of homogenate was pipetted; 5 μl of 10*RIPA lysis solution (CST) and protease inhibitor (Beyotime) were added and mixed well; the lysis was performed for 30 min on ice; after 30 min of centrifugation at 15000 g at 4° C., the supernatant was collected for protein quantification and WB detection.

Vector Genome Copy Number Analysis

5 μl of DNA detection sample was taken. 45 μl of sample diluent (5 μl of Pluronic F68 (Gibco, 24040032) and 2 μl of tRNA (Ambion, AM7119) were added in 1 ml of RNA enzyme-free water. After mixing well, 5 μl of the diluent was aspirated, added with 45 μl of the sample diluent, and mixed well to obtain a 100-fold diluted DNA sample to be tested. Plotting of standard curves was performed with a linearized and absolutely quantified plasmid (pAAV-CMV-EGFP) as a standard. The qPCR reaction solution was prepared according to the following reaction system: Taqman PCR Mix, upstream primer (10 μM), downstream primer (10 μM), probe (10 μM), DNA template. The qPCR reaction was carried out under the following reaction conditions: 50° C., 2 min; 95° C., 10 min; 95° C., 15 s, 60° C., 30 s, 40 cycles; 37° C., 2 s. At the end of the reaction, a standard curve was prepared according to the Ct value of the standard, and the Vg number of each sample to be tested was calculated by linear regression.

Mouse OCT Assay

Optical coherence tomography (OCT) examination: the anesthetized animal was placed on a lifting platform, subjected to conventional mydriasis by using compound tropicamide eye drops, and subjected to topical anesthesia by using proparacaine hydrochloride eye drops. The eye position was placed. After mydriasis, medical carbomer eye drops gel was applied to the cornea of the eye to be tested. The light source of the ophthalmic ultramicroscopic imaging system was adjusted and focused. The lens was adjusted to focus on the retina to perform optical coherence tomography (OCT) on the retina. Photographs were taken of both eyes of each experimental animal. After completion of the experiment, both eyes were washed with normal saline, and levofloxacin eye drops were used to prevent infection.

Mouse ERG Assay

The mice to be tested were placed in the dark room and reared for 3 days to reach the experimental time point. The mice were subjected to waveform acquisition of electroretinogram (ERG) in the dark room. After the mice were anesthetized and mydriasis, 0.25% hydroxypropyl methylcellulose solution was injected into both eyes to protect the cornea. The mice were placed on the operating table with a heating pad. A red metal wire electrode was inserted under the skin epidermis at the center between the two eyes of the mice, and a black ground electrode was inserted under the tail epidermis of the mice. The ERG images were collected by an electroretinogram Ganzfeld ERG system (Micron IV, Phoenix Research Laboratories, Inc), which is automatically analyzed by the software in the system to obtain the average amplitude of a-wave and b-wave for each stimulation intensity for statistical analysis. The waveform of electroretinogram can reflect the conduction function of retinal neurons, and the measured waveform mainly consists of negative a-wave and positive b-wave, wherein the a-wave reflects the function of primary retinal neurons, namely photoreceptor cells, and the b-wave reflects the function of secondary retinal neurons, namely bipolar cells.

EXAMPLES

Example 1: Construction and Isolation and Purification of Adenoviral Vector 1.1 Construction of Adenoviral Vector The structure of the CYP4V2 expression cassette is shown in FIG. 1. The CYP4V2 expression cassette comprises, from the 5' to the 3' end, a 5' ITR, a CMV enhancer, a CBA promoter, a CBA exon 1 & intron 1, a Kozak sequence, and a gene of interest: wild-type human CYP4V2 gene hCYP4V2 WT or optimized CYP4V2 gene hCYP4V2 opt, BGH polyA) and 3' ITR. wherein:

The nucleotide sequence of 5' ITR is shown as SEQ ID NO: 1;

The CMV enhancer is a cytomegalovirus (CMV) enhancer element, the nucleotide sequence of which is shown in SEQ ID NO: 2;

The CBA promoter is a chicken β-actin gene promoter, the nucleotide sequence of which is shown in SEQ ID NO: 3;

CBA exon 1 & intron 1 is the first exon and the first intron of the chicken β-actin gene, the nucleotide sequence of which is shown in SEQ ID NO: 4;

The hCYP4V2WT gene was derived from the wild-type human CYP4V2 gene (Gene ID: 285440), the gene sequence of which is shown in SEQ ID NO: 9, and the wild-type hCYP4V2 WT protein encoded by it has an NCBI accession number of NP_997235.3.

Optimized CYP4V2 gene hCYP4V2 opt are codon-optimized genes opt18, opt7, opt8, and opt6 encoding the wild-type hCYP4V2 WT protein, and the nucleotide sequences are SEQ ID NO: 5, SEQ ID NO: 6, SEQ ID NO: 7 and SEQ ID NO: 8 respectively.

BGH polyA is a bovine growth hormone polyadenylation signal, the nucleotide sequence of which is shown as SEQ ID NO: 10.

The nucleotide sequence of 3' ITR is shown as SEQ ID NO. 11.

The Kozak sequence is inserted in front of the CYP4V2 cDNA sequence, for example, SEQ ID NO: 17 (GCCACC).

The expression cassette comprising the wild-type human CYP4V2 gene hCYP4V2WT was constructed as plasmid pAAV2-CYP4V2 WT.

The expression cassette containing the optimized CYP4V2 gene was constructed as plasmid pAAV2-CYP4V2 opt. Among them, SEQ ID NO: 12 shows the nucleotide sequence of the expression cassette comprising the codon-optimized gene opt6; SEQ ID NO: 13 shows the nucleotide sequence of the expression cassette comprising the codon-optimized gene opt7; and SEQ ID NO: 14 shows the nucleotide sequence of the expression cassette comprising the codon-optimized gene opt8; the nucleotide sequence of the expression cassette comprising the codon-optimized gene opt18 is shown in SEQ ID NO: 15. The nucleotide sequence of the expression cassette comprising CYP4V2 WT is shown in SEQ ID NO: 16.

The CYP4V2 expression cassette may be packaged in rAAV with a vector having a capsid from any of the AAV serotypes or hybrids or variants thereof.

Viral vectors are obtained by the plasmid co-transfection method. The HEK 293T cells were co-transfected with a helper plasmid containing the AAV2 coat protein gene and a gene that can facilitate AAV replication and a shuttle plasmid pAAV2-CYP4V2 WT or plasmid pAAV2-CYP4V2 opt containing an expression cassette for CYP4V2 gene of interest to form a recombinant adeno-associated virus vector.

1.2 Isolation and Purification of Adenoviral Vector

The production of AAV vector uses a three-plasmid system, i.e. a shuttle plasmid containing the target gene CYP4V2, a pRepCap plasmid with the repcap gene of the AAV vector, and a helper plasmid pHelper, and uses PEI as a transfection reagent to co-transfect HEK293 cells and recombine to package an AAV virus vector. Harvesting was performed 48-72 hours after transfection. The harvest solution was purified by affinity chromatography, further purified by anion chromatography, and concentrated by ultrafiltration. The buffer was replaced. The purified recombinant AAV virus vector was subjected to genome titer determination, sterilization, filtering, and dispensing for future use.

Example 2: In Vitro Expression Assay of Codon-Optimized CYP4V2 Opt

This example evaluated the in vitro expression levels of codon-optimized CYP4V2 opt in two cell lines, HEK293 and ARPE-19. Among them, HEK293 cell line was transfected with plasmid and ARPE-19 cell line was infected with AAV virus to introduce the gene of interest into cells.

Figure 2:
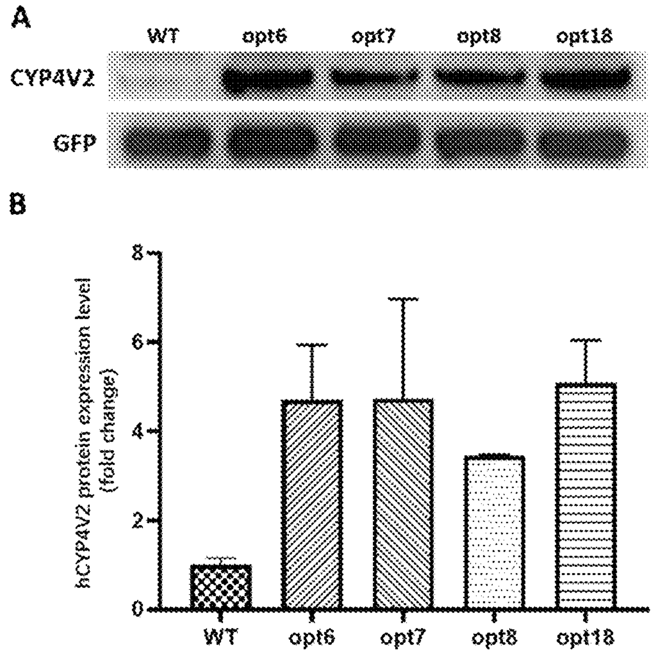
FIG. 2 shows the in vitro expression of a codon-optimized CYP4V2 opt gene in plasmid-transfected HEK293 cells. Wherein, (A) a representative image of a CYP4V2 protein Western blot; (B) quantification of CYP4V2 protein Western blot to detect expression levels of CYP4V2 and GFP (plasmid-transfected control) expressed in HEK293 cells with WT or opt genes and GFP expressed using CAG-CYP4V2 WT/opt and CMV-EGFP dual plasmid. Cell lysates were harvested 2 days after transfection of equal amounts of plasmids. Equal amounts of total protein were separated by SDS-PAGE and then immunoblotted. Expression levels of CYP4V2 were normalized with GFP and calculated as a ratio to WT expression level.

Both plasmid AAV2-CYP4V2 WT expressing CYP4V2 WT or plasmid AAV2-CYP4V2 opt expressing CYP4V2 opt were transiently transfected in HEK293 and protein expression in cell lysates was assessed by Western blot analysis (FIG. 2). The expression levels of opt6, opt7, opt8, opt18 (SEQ ID NO: 8, 6, 7, 5) of CYP4V2 gene after codon optimization in HEK293 cells were significantly higher than that of wild-type human CYP4V2 gene (WT).

Figure 3:
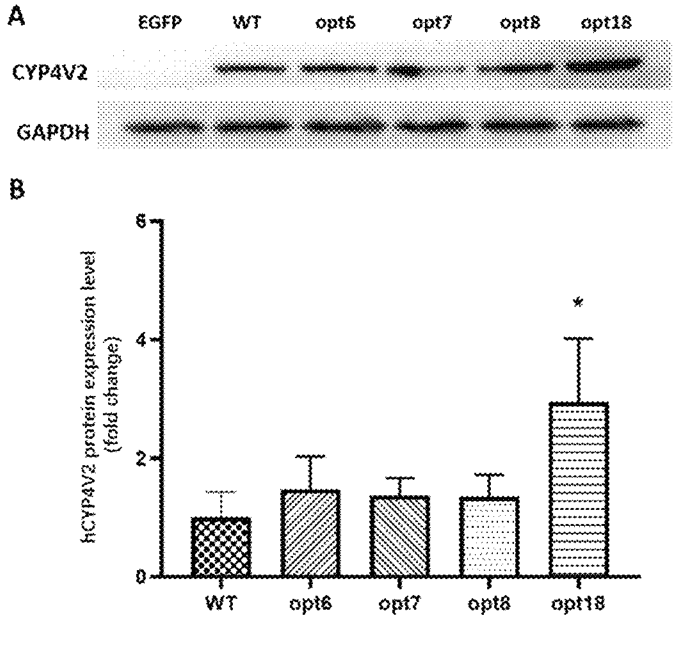
FIG. 3 shows the in vitro expression of codon-optimized CYP4V2 in AAV2-transfected ARPE-19 cells. Wherein, (A) a representative image of a CYP4V2 protein Western blot; (B) quantification of CYP4V2 protein Western blot to detect expression levels of CYP4V2 and GAPDH (internal control) in ARPE-19 cells, wherein WT or opt gene or the EGFP control was mediated with equal amounts of AAV2 viral particles (MOI=20000). Cell lysates were harvested 2 days after virus particle infection. Equal amounts of total protein were separated by SDS-PAGE and then immunoblotted. The expression level of CYP4V2 was normalized to GAPDH and calculated as a ratio to the WT expression level (compared to WT expression level: *, $p<0.05$; **, $p<0.01$; N=3, student test).

Protein expression in cell lysates was assessed by Western blot analysis following infection with plasmid AAV2-CYP4V2 WT or plasmid AAV2-CYP4V2 opt in ARPE-19 (FIG. 3).

As can be seen from FIGS. 2 and 3, the codon-optimized CYP4V2 opt gene, in particular opt18, showed significantly higher expression levels compared to the wild-type human CYP4V2 WT gene.

Example 3: Construction and Characterization of the BCD Cell Model

Figure 4:
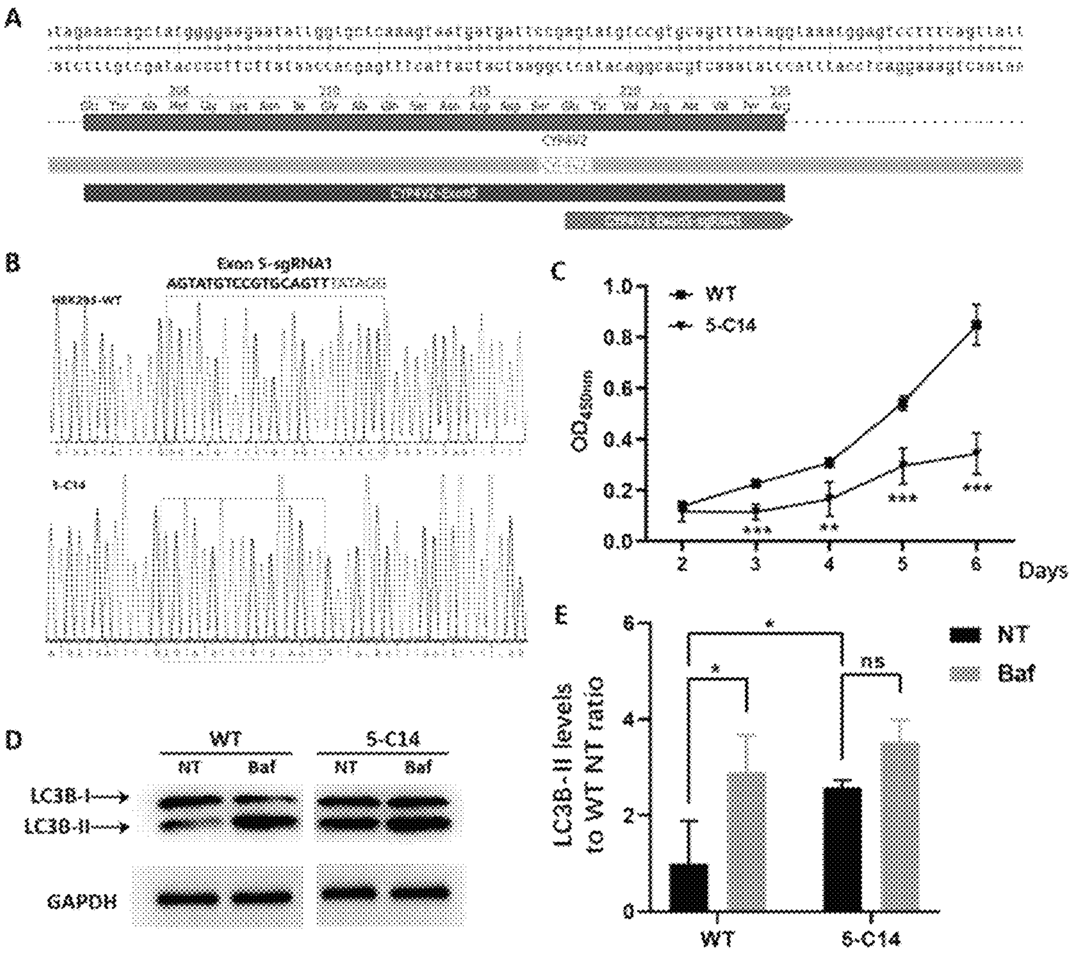
FIGS. 4-6 show the in vitro potency of AAV2-CYP4V2 in the BCD cell model.
Figure 5:
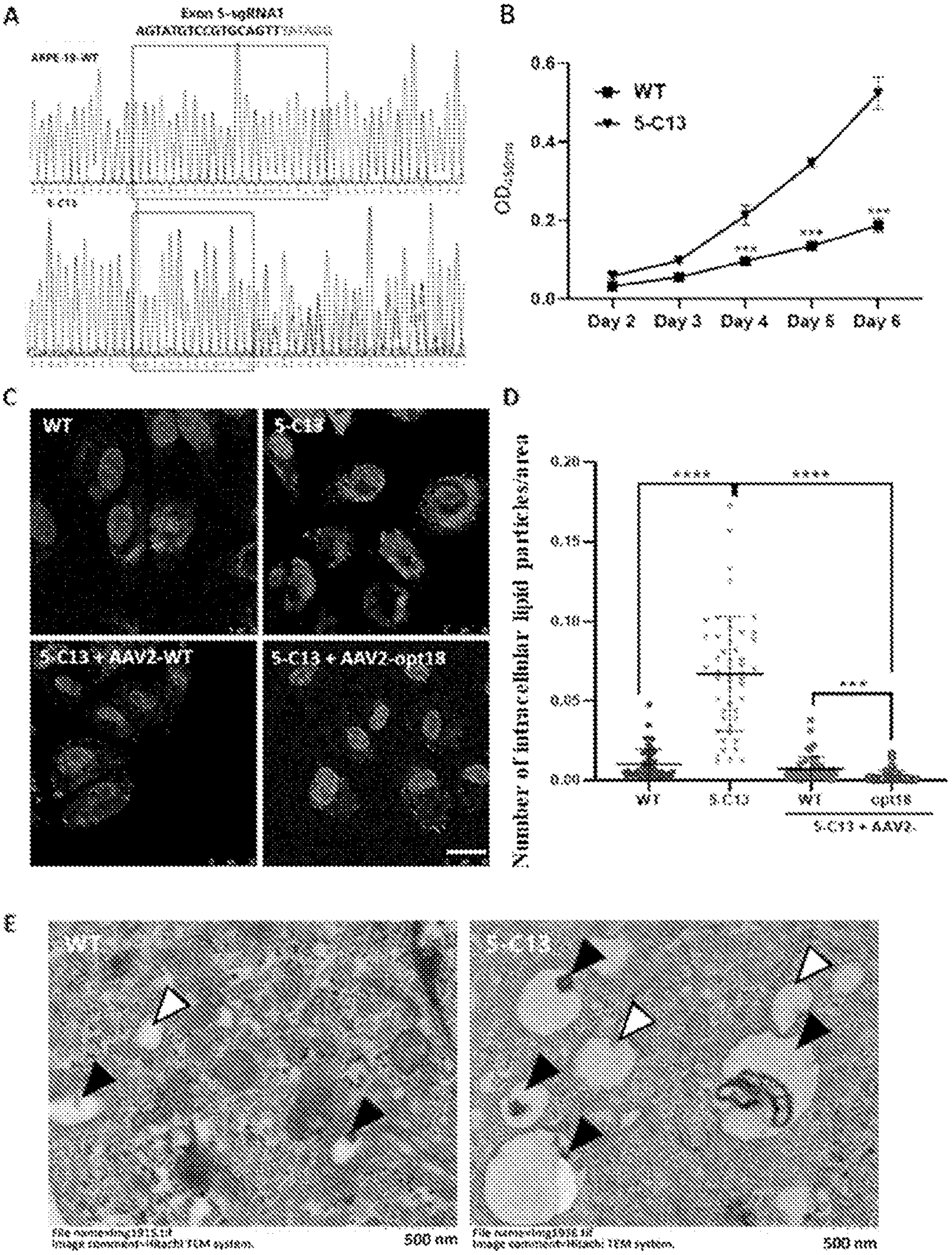

To assess the efficacy of AAV2-CYP4V2 WT and opt genes in BCD gene therapy, this example used the CRISPR-Cas9 method to construct cell models with CYP4V2 mutation in both HEK293 and ARPE-19 cell lines (FIGS. 4 and 5).

The strategy for constructing the cell model is shown in FIG. 4A. Exon5-sgRNA1 (the nucleotide sequence thereof is shown in Table 1) was designed around Exon5; Exon7-sgRNA1, Exon7-sgRNA2, and Exon7-sgRNA3 (the nucleotide sequence thereof is shown in Table 1 respectively) were designed around Exon7; all four sgRNA were constructed into a Cas9-sgRNA vector (Addgene, #58766) to obtain a Cas9-sgRNA plasmid. The Cas9-sgRNA plasmid was transiently transfected into HEK293 and ARPE-19 cells, respectively. 48 H after transfection, puromycin was added to remove the unsuccessfully transfected cells. The cells were then seeded into 96-well culture plates by limiting dilution method and cultured. Two to three weeks later, the genotype of monoclonal cells in the 96-well plate was identified by PCR. The primer sequences used are detailed in Table 1.

TABLE 1

| sgRNA and Primer Sequences Used in the Construction of CYP4V2 Mutant Cells with CRIPSR/Cas9 | | |
|---|---|---|
| Name | Sequence | Use |
| CYP4V2-Exon5-sgRNA1 | agtatgtccgtgcagtttatagg (SEQ ID NO: 18) | sgRNA vector construction |
| CYP4V2-Exon7-sgRNA1 | catacaggtcatcgctgaacggg (SEQ ID NO: 19) | |
| CYP4V2-Exon7-sgRNA2 | tcatacaggtcatcgctgaacgg (SEQ ID NO: 20) | |
| CYP4V2-Exon7-sgRNA3 | gattatcattcaaatcatacagg (SEQ ID NO: 21) | |
| CYP4V2-Exon5-F | gaaatcacactccaccggga (SEQ ID NO: 22) | GenomeDNA PCR |
| CYP4V2-Exon5-R | acctttactgcttaaacacatgct (SEQ ID NO: 23) | |
| CYP4V2-Exon7-F | caggcagcagaaatcgcaag (SEQ ID NO: 24) | |
| CYP4V2-Exon7-R | agcctgttcccttcgtcatc (SEQ ID NO: 25) | |
| CYP4V2-ssDNA | taactagggtgcatccaagtccaaacagaagcatgtgattatcattcaaagcgaacgggccaatgaaatgaacgccaatgaagactgtagaggtgatggcag (SEQ ID NO: 26) | Homologous recombination repair template |

After screening and amplification of monoclonal cells, cell clones with the correct mutations were verified by gene sequencing, and the results are shown in FIGS. 4B and 5A. The genotypes of the cell clones and the protein product are described in Table 2. The full-length sequence of the wild-type CYP4V2 protein is shown as SEQ ID NO: 27 and its nucleotide sequence as SEQ ID NO: 28. The mutant cells of exon 5 of CYP4V2 had frameshift mutation at 223-224aa of the full-length sequence, and the mutant cells of exon 7 had frameshift mutation at 268-271aa, and expressed a truncated protein compared to the wild type.

TABLE 2

| Construction of CYP4V2 mutant cells with CRIPSR/Cas9 | | | | |
|---|---|---|---|---|
| Mutant | Clone number | Allele | Genome | Predicted protein |
| HEK293-CYP4V2 mutant 1 | Exon 5-C6 | Allele 1/2 | 668 del T | Frameshift mutation started at 224aa, ended at 226aa |
| HEK293-CYP4V2 mutant 2 | Exon 5-C14 | Allele 1/2 | 670~673 del 4 ins 67 bp | Frameshift mutation started at 223aa, ended at 237aa |
| HEK293-CYP4V2 mutant 3 | Exon7-C8 | Allele 1/2 | 814 ins 162 bp | Frameshift mutation started at 272aa, ended at 292aa |
| HEK293-CYP4V2 mutant 4 | Exon7-C30 | Allele 1/2 | Intron 6 del 8, 802-810 del 9 | 268aa~329aa delete |
| ARPE-19-CYP4V2 mutant 1 | Exon 5-C13 | Allele 1 | 667~674 del 8 intron del 5 | Frameshift mutation started at 223aa, ended at 226aa |
| | | Allele 2 | 668 del T | Frameshift mutation started at 224aa, ended at 226aa |
| ARPE-19-CYP4V2 mutant 2 | Exon 5-C26 | Allele 1 | 668 del T | Frameshift mutation started at 224aa, ended at 226aa |
| | | Allele 2 | 671~672 del AT | Frameshift mutation started at 224aa, ended at 224aa |
| ARPE-19-CYP4V2 mutant 3 | Exon 5-C27 | Allele 1 | 668 del T | Frameshift mutation started at 224aa, ended at 226aa |
| | | Allele 2 | 671~672 del AT | Frameshift mutation started at 224aa, ended at 224aa |
| ARPE-19-CYP4V2 mutant 4 | Exon 7-C26 | Allele 1 | 810 del T | Frameshift mutation started at 271aa, ended at 276aa |
| | | Allele 2 | 812~813 del AA | Frameshift mutation started at 271aa, ended at 274aa |

HEK293 cells having the CYP4V2 mutation were phenotypically characterized by measuring cell proliferation and autophagosome function. It has been reported in the literature that there is a decrease in cell proliferation rate and loss of autophagosome function in RPE cells differentiated from iPSC cells of BCD patients. The present inventors found that the cell proliferation rate of HEK293 mutant cells was significantly reduced compared to HEK293 WT cells. The present inventors evaluated protein levels of the autophagosome marker microtubule-associated protein 1 light chain 3 (LC3) in HEK293 WT and mutant cells. C-terminal processing of LC3 protein can produce LC3-I. Modifications are initiated during autophagosome formation, changing LC3-I to LC3-II. The results showed that the expression level of LC3-II protein was higher in HEK293 mutant cells than in HEK293 WT cells. Bafilomycin-A1, a vacuolar H+-ATPase inhibitor, can increase LC3-II protein levels in WT cells but not in mutant cells. This indicates autophagosome accumulation but impaired autophagy flux in mutant cells. These observations suggest that the CYP4V2 mutation causes a loss of normal cell function, resulting in decreased cell proliferation and defective autophagosome function in HEK293 cells (FIGS. 4C-E). FIG. 4 shows the identification results as represented by 5-C14 cells. Other cell clones had similar phenotypic results.

In the ARPE-19 cell line, which is characterized more closely to RPE cells, the CYP4V2 mutation also causes a change in the cell phenotype. ARPE-19 cells are derived from human retinal pigment epithelial cells that express the surface markers CRALBP and RPE-65 of RPE cells. CYP4V2 mutant ARPE-19 cells were obtained by using CRISPR-Cas9 technology (FIG. 5A). Compared with ARPE-19 WT cells, ARPE-19 mutant cells showed significantly reduced cell proliferation rate (FIG. 5B). CYP4V2 gene encodes hydroxylase involved in fatty acid metabolism in ocular RPE cell layer, and maintains the steady-state balance of retinal polyunsaturated fatty acids. In the CYP4V2 mutant ARPE-19 cell line, fat particle deposition was significantly higher in cells treated with 160 μM arachidonic acid (AA) for 4 consecutive days followed by staining with 5 μM BODIPY 493/503 lipid than in wild-type cells (FIGS. 5C-5D). Transmission electron microscopy revealed a greater number of autophagy vacuoles in the mutant cells (FIG. 5E). These observations suggest that the CYP4V2 mutation causes a loss of normal cell function, resulting in decreased cell proliferation, abnormal fat metabolism, and defective autophagosome function in ARPE-19 cells. FIG. 5 shows the identification results as represented by 5-C13 cells.

Example 4: In Vitro Pharmacodynamic Evaluation of Codon-Optimized AAV2-CYP4V2 Opt in BCD Cell Model The in vitro potency of codon-optimized CYP4V2 opt was assessed in two BCD cell models, HEK293 and ARPE-19 having the CYP4V2 mutation, following infection with the AAV virus. AAV2 mediated expression of CYP4V2 WT and opt in the HEK293 CYP4V2 mutated BCD cell model is shown in FIG. 6A. The expression of CYP4V2 opt was higher than that of WT under the same amount of virus infection.

Expression of CYP4V2 WT and opt repaired the cell proliferation rate defect of mutant cells in HEK293 BCD cell model in a dose-dependent manner (FIGS. 6B-C). The level of cell proliferation following functional repair of mutant cells by CYP4V2 opt was still lower than that of wild type HEK293 cells, indicating that expression of CYP4V2 opt did not overactivate the cells (FIG. 6D).

Consistent with the decreased proliferation of partially repaired cells, expression of CYP4V2 WT and opt also partially restored the autophagosome function defect of mutant cells. Expression of AAV2-CYP4V2 WT or opt in mutant cells did not significantly repair autophagosome accumulation compared to EGFP controls (without the addition of Baf treatment: NT conditions). However, autophagy flux was significantly increased in mutant cells expressing AAV2-CYP4V2 WT or opt upon treatment with Bafilomycin-A1 (Baf), indicating that autophagy function was partially restored (FIGS. 6E-F).

Similarly, AAV2 mediated CYP4V2 WT and opt showed a therapeutic effect in the ARPE-19 BCD cell model with CYP4V2 mutation. ARPE-19 mutant cells 5-C13 were infected by AAV2-WT and AAV2-opt18 viruses, as shown in FIGS. 5C-5D. In ARPE-19 mutant cells 5-C13 infected with AAV2 WT and AAV2 opt18 viruses, compared with uninfected mutant cells, lipid deposition particles were significantly reduced, reaching the level of wild-type ARPE-19 cells. The optimized gene opt18 has a better effect on reducing lipid deposition compared to WT, with significant statistical differences. (FIGS. 5C-5D).

Figure 6:
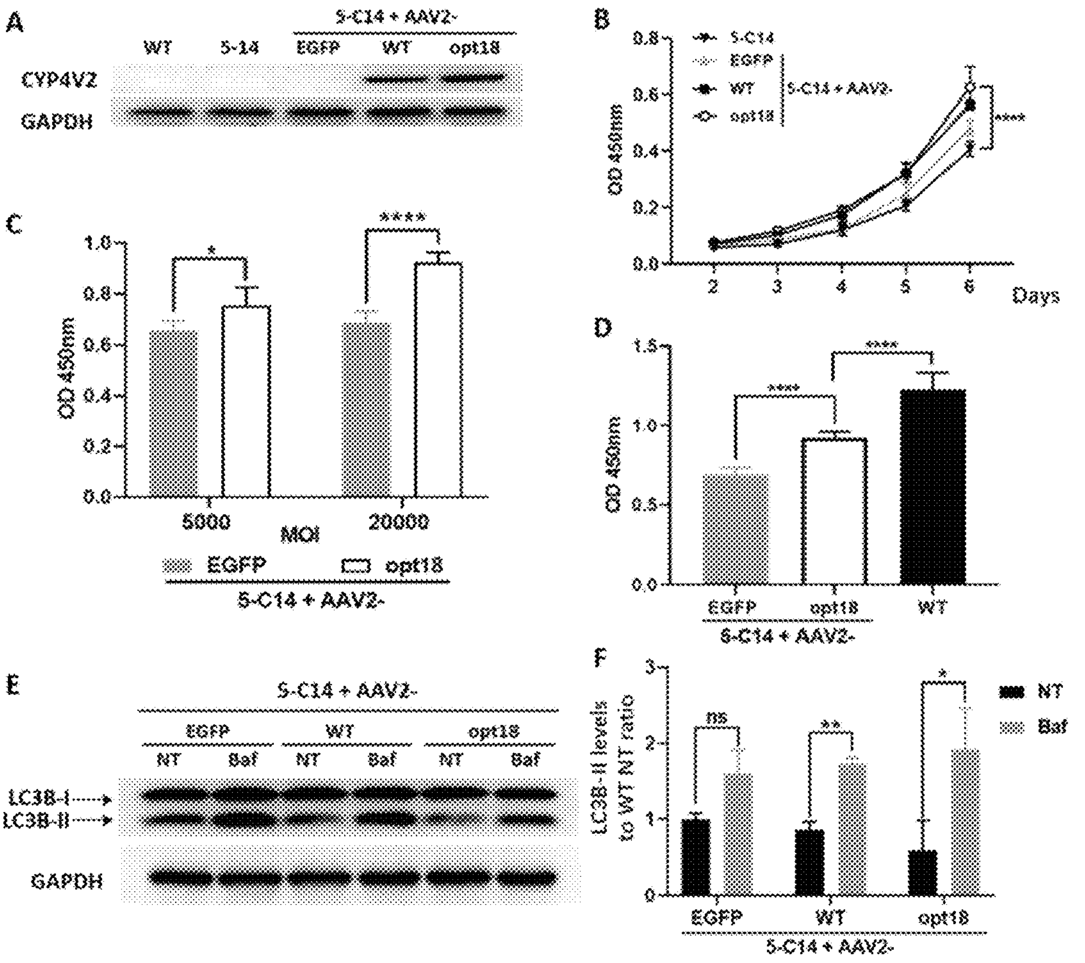

FIGS. 5-6 show the results as represented by CYP4V2 opt18. Similar phenotypic results were observed for the expression of other opt genes.

These results indicate that the phenotypic defect observed in the HEK293 and ARPE-19 BCD cell models is caused by a loss of function of the CYP4V2 gene. Supplementation of the expression of the CYP4V2 gene can restore functional defects in these cells and has the effect of treating BCD.

Example 5: In Vivo Expression Assay of Codon-Optimized CYP4V2 Opt

Figure 7:
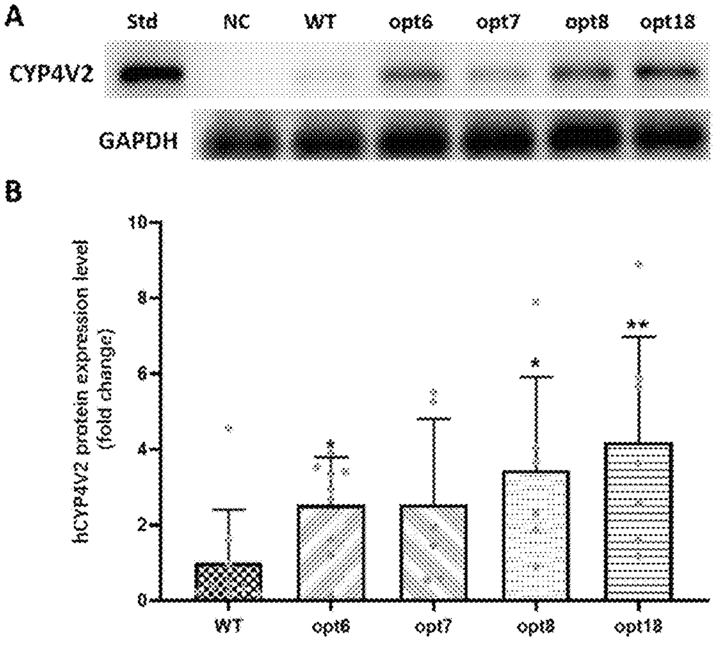
FIG. 7 shows in vivo expression of codon-optimized AAV-CYP4V2 in mouse eyes by subretinal injection. (A) AAV2-CYP4V2 wild-type and optimized gene expression in mouse eyes. Wild-type mouse eyeballs were injected through the subretinal space with 1 ul of $5\times10^{12}$ vg/ml AAV2-CYP4V2 WT or opt recombinant viral particles. After 4 weeks, eye tissues were taken. The retinas were isolated and homogenized for lysis. Equal amounts of total protein were separated by SDS-PAGE and then immunoblotted. (A) Representative image of CYP4V2 protein Western blot; (B) Quantification of CYP4V2 protein Western blot to detect expression levels of CYP4V2 and GAPDH (internal control), the expression level of CYP4V2 being normalized to GAPDH and calculated as a ratio to WT expression level (compared to WT expression level: *, $p<0.05$; student test; n=6-9). Std: purified recombinant human CYP4V2 protein standard sample. NC: an uninjected mouse eyeball negative control.

Four-week-old wild-type C57BL/6 mice were injected with 1 μl of $1.5\times10^{12}$ vg/ml AAV2-CYP4V2 WT and opt recombinant virus particles via subretinal cavity injection. Ocular tissues were sampled every 4 weeks after injection. After homogenizing the mouse eye tissue, RIPA lysate was added to lyse the tissue, and the homogenate was lysed. Equal amounts of total protein were separated by SDS-PAGE, then immunoblotted. CYP4V2 expression levels were detected by Western after protein quantification. Expression levels of the genes were analyzed by Western blot detection. The protein expression level of the CYP4V2 opt gene after codon optimization was compared with WT. The results at 4 weeks post-injection showed that the AAV2-CYP4V2 opt gene was expressed at higher levels in mouse eyes than in WT (FIG. 7).

Example 6: Phenotypic Characterization of the High Fat-Fed CYP 4V3 KO BCD Mouse Model The knockout (KO) model of the mouse CYP4V3 gene, which is homologous to the human CYP4V2 gene, has fewer physiological and functional changes compared to BCD patients, and the phenotype appears much later than in patients. Six-month-old mice (equivalent to 20-30 years of age in humans) had sporadic ocular lipid deposits, and 12-month-old mice (equivalent to 50 years of age in humans, already suffering from ocular blindness) had significant lipid deposits without ocular ERG function and loss of vision (Lockhart, C. M., et al. (2014). "Generation and character ization of a murine model of Bietti crystalline dystrophy." Invest Ophthalmol Vis Sci 55(9): 5572-5581). The occurrence of retinopathy was accelerated and aggregated in the CYP4V3 KO mouse model after administration of a high-fat diet (HFD) (Qu, B., et al. (2020). "Treating Bietti crystalline dystrophy in a high-fat diet-exacerbated murine model using gene therapy." Gene Ther 27(7-8): 370-382). In this example, HFD feeding was performed after birth and weaning. Fundus imaging, OCT, and ERG functional tests were performed every 4 weeks after 4 weeks of age.

Example 7: In Vivo Pharmacodynamic Evaluation of Codon-Optimized AAV2-CYP4V2 Opt in BCD Mouse Model 1 μl of $5e^{12}$ vg/ml AAV2-GFP or CYP4V2 opt virus particles were injected in the eyeballs of high-fat fed CYP4V3 KO BCD mice with pathological changes of the ocular fundus using subretinal space injection. OCT and ERG functional tests were performed every 4 weeks after injection, and the therapeutic effects of AAV2-GFP and CYP4V2 opt virus particles were compared and analyzed.

The invention claimed is:

1. A polynucleotide encoding a CYP4V2 protein, wherein the polynucleotide comprises the nucleotide sequence as shown in SEQ ID NO: 5.

2. An expression cassette comprising the polynucleotide of claim 1 and a promoter operably linked to the polynucleotide.

3. An expression vector comprising the polynucleotide of claim 1 an expression cassette comprising the polynucleotide of claim 1.

4. The expression vector of claim 3, further comprising an expression control element to which the polynucleotide encoding the CYP4V2 protein is operably linked.

5. The expression vector of claim 4, wherein the expression control element is selected from one or more of an origin of replication, a promoter, an enhancer, an intron, a polyA signal, ITR, an insulator.

6. The expression vector of claim 3, wherein the expression vector further comprises an origin of replication.

7. The expression vector of claim 6, wherein the origin of replication sequence is selected from f1 bacteriophage ori, RK2oriV, pUC on or pSC101ori.

8. The expression vector of claim 3, wherein the expression vector further comprises a 5' ITR.

9. The expression vector of claim 8, wherein the nucleotide sequence of the 5' ITR is as shown in SEQ ID NO: 1.

10. The expression vector of claim 3, wherein the expression vector further comprises a 3' ITR.

11. The expression vector of claim 10, wherein the nucleotide sequence of the 3' ITR is as shown in SEQ ID NO: 11.

12. The expression vector of claim 3, wherein the expression vector further comprises an enhancer.

13. The expression vector of claim 12, wherein the enhancer is a CMV enhancer.

14. The expression vector of claim 13, wherein the nucleotide sequence of the enhancer is as shown in SEQ ID NO: 2.

15. The expression vector of claim 3, wherein the expression vector further comprises a promoter.

16. The expression vector of claim 15, wherein the promoter is a specific or non-specific promoter.

17. The expression vector of claim 16, wherein the promoter is selected from a Chicken Beta-Actin (CBA)

promoter, CMV promoter, SV40 promoter, human phosphoglycerate kinase (hPGK) promoter and a version of 3rd-generation Tet-responsive (TRE3GS) promoter.

18. The expression vector of claim 17, wherein the promoter is a CBA promoter.

19. The expression vector of claim 18, wherein the nucleotide sequence of the CBA promoter is as shown in SEQ ID NO: 3.

20. The expression vector of claim 15, wherein the promoter is an inducible promoter.

21. The expression vector of claim 20, wherein the inducible promoter comprises one or more of a tetracycline-regulated promoter, an alcohol-regulated promoter, a steroid-regulated promoter, a metal-regulated promoter, a pathogen-regulated promoter, a temperature/heat-inducible promoter, a light-regulated promoter, and a IPTG-inducible promoter.

22. The expression vector of claim 21, wherein the tetracycline-regulated promoter is selected from a Tet on promoter, a Tet off promoter, or a Tet Activator promoter.

23. The expression vector of claim 21, wherein the alcohol-regulated promoter is selected from an alcohol dehydrogenase I (alcA) gene promoter, or a promoter responsive to an alcohol transactivator protein (AlcR).

24. The expression vector of claim 21, wherein the steroid-regulated promoter is selected from a rat glucocorticoid receptor promoter, a human estrogen receptor promoter, a moth ecdysone receptor promoter, a retinoid promoter, or a thyroid receptor superfamily promoter.

25. The expression vector of claim 21, wherein the metal-regulated promoter is selected from yeast, mouse or human metallothionein promoters.

26. The expression vector of claim 21, wherein the pathogenic-regulated promoter is selected from a salicylic acid-regulated promoter, an ethylene-regulated promoter or a Benzothiadiazole-regulated (BTH) promoter.

27. The expression vector of claim 21, wherein the temperature/heat inducible promoter is selected from an HSP-70 promoter, an HSP-90 promoter, or a soybean heat shock promoter.

28. The expression vector of claim 21, wherein the light-regulated promoter is a light-responsive promoter of a plant cell.

29. The expression vector of claim 3, wherein the expression vector further comprises an exon and an intron.

30. The expression vector of claim 29, wherein the exon and intron are the first exon and first intron of the chicken β-actin gene.

31. The expression vector of claim 30, wherein the nucleotide sequence of the exon and intron is as shown in SEQ ID NO: 4.

32. The expression vector of claim 3, wherein the expression vector further comprises a polyA signal.

33. The expression vector of claim 32, wherein the polyA signal is bovine growth hormone poly A, SV40 polyA, or human beta globin poly A.

34. The expression vector of claim 33, wherein the nucleotide sequence of the polyA signal is as shown in SEQ ID NO: 10.

35. The expression vector of claim 3, wherein the nucleotide sequence of the expression vector is as shown in SEQ ID NO: 12, SEQ ID NO: 13, SEQ ID NO: 14, SEQ ID NO: 15, or SEQ ID NO: 16.

36. The expression vector of claim 3, wherein the expression vector further comprises a post-transcriptional regulatory element.

37. The expression vector of claim 36, wherein the post-transcriptional regulatory element is a woodchuck hepatitis virus post-transcriptional regulatory element.

38. The expression vector of claim 3, wherein the expression vector further comprises a gene encoding a marker.

39. The expression vector of claim 38, wherein the marker is selected from one or more of an antibiotic resistance protein, a toxin resistance protein, a colored or fluorescent protein.

40. The expression vector of claim 39, wherein the antibiotic is selected from ampicillin, neomycin, G418, puromycin and blasticidin.

41. The expression vector of claim 39, wherein the toxin is selected from anthrax toxin and diphtheria toxin.

42. The expression vector of claim 39, wherein the colored or fluorescent protein is selected from a green fluorescent protein, an enhanced green fluorescent protein, and a red fluorescent protein.

43. The expression vector of claim 38, wherein the marker is dihydrofolate reductase.

44. The expression vector of claim 4, wherein the expression vector is a plasmid.

45. The expression vector of claim 4, wherein the expression vector is a cosmid.

46. The expression vector of claim 4, wherein the expression vector is a viral vector.

47. The expression vector of claim 4, wherein the expression vector is an RNA vector.

48. The expression vector of claim 4, wherein the expression vector is a linear or circular DNA or RNA molecule.

49. The expression vector of claim 44, wherein the plasmid is selected from pCI, puc57, pcDNA3, pSG5, pJ603, and pCMV.

50. The expression vector of claim 46, wherein the viral vector is selected from retrovirus, adeno-associated virus, coronavirus, influenza virus, rabies virus, vesicular stomatitis virus, measles virus, Sendai virus, alphaviruses, herpes simplex virus types 1 and 2, Epstein-Bar virus, cytomegalovirus, cowpox virus, fowlpox virus, and canarypox virus, norwalk virus, togavirus, flavivirus, reovirus, papovavirus, hepadnavirus, baculovirus, and hepatitis virus.

51. The expression vector of claim 46, wherein the viral vector is a picornavirus.

52. The expression vector of claim 50, the retrovirus is selected from mammalian C-type, lentivirus and spumavirus.

53. The expression vector of claim 52, wherein the lentiviral vector is selected from HIV-1, HIV-2, SIV, FIV, BIV, EIAV, CAEV and ovine demyelinating leukoencephalitis lentivirus.

54. The expression vector of claim 50, wherein the expression vector is an adeno-associated virus.

55. The expression vector of claim 54, wherein the adeno-associated virus is selected from AAV type 1, AAV type 2, AAV type 3, AAV type 4, AAV type 5, AAV type 6, AAV type 7, AAV type 8, AAV type 9, and AAV type 10.

56. The expression vector of claim 3, wherein the expression vector further comprises a shortened chimeric intron and a Kozak initiation sequence.

57. The expression vector of claim 56, wherein the shortened chimeric intron is as shown in SEQ ID NO: 4.

58. The expression vector of claim 56, wherein the nucleotide sequence of the Kozak initiation sequence is as shown in SEQ ID NO: 17.

59. A viral particle comprising the polynucleotide of claim 1.

60. A viral particle comprising the expression cassette of claim 2.

61. A viral particle comprising the expression vector of claim 3.

62. A pharmaceutical composition for the treatment of Bietti crystalline dystrophy (BCD) comprising the polynucleotide of claim 11 and a pharmaceutically acceptable carrier, wherein the pharmaceutical composition expresses wild type or codon-optimized CYP4V2 protein.

63. A method for treating Bietti crystalline dystrophy in a mammalian subject, comprising administering to the subject via subretinal injection of an effective amount of the polynucleotide of claim 1.

64. A method for treating Bietti crystalline dystrophy in a mammalian subject, comprising administering to the subject via subretinal injection of an effective amount of the pharmaceutical composition of claim 62.

* * * * *

SEQUENCE LISTING

```
Sequence total quantity: 28
SEQ ID NO: 1            moltype = DNA  length = 145
FEATURE                 Location/Qualifiers
source                  1..145
                        mol_type = other DNA
                        organism = synthetic construct
SEQUENCE: 1
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcct                                        145

SEQ ID NO: 2            moltype = DNA  length = 380
FEATURE                 Location/Qualifiers
source                  1..380
                        mol_type = other DNA
                        organism = synthetic construct
SEQUENCE: 2
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg                                              380

SEQ ID NO: 3            moltype = DNA  length = 278
FEATURE                 Location/Qualifiers
source                  1..278
                        mol_type = other DNA
                        organism = synthetic construct
SEQUENCE: 3
tcgaggtgag ccccacgttc tgcttcactc tccccatctc ccccccctcc ccacccccaa  60
ttttgtattt atttattttt taattatttt gtgcagcgat gggggcgggg gggggggggg  120
ggcgcgcgcc aggcggggcg gggcggggcg aggggcgggg cggggcgagg cggagaggtg  180
cggcggcagc caatcagagc ggcgcgctcc gaaagtttcc ttttatggcg aggcggcggc  240
ggcggcggcc ctataaaaag cgaagcgcgc ggcgggcg                          278

SEQ ID NO: 4            moltype = DNA  length = 1017
FEATURE                 Location/Qualifiers
source                  1..1017
                        mol_type = other DNA
                        organism = synthetic construct
SEQUENCE: 4
ggagtcgctg cgcgctgcct tcgccccgtg ccccgctccg ccgccgcctc gcgccgcccg  60
ccccggctct gactgaccgc gttactccca caggtgagcg ggcgggacgg cccttctcct  120
ccgggctgta attagcgctt ggtttaatga cggcttgttt cttttctgtg gctgcgtgaa  180
agccttgagg ggctccggga gggccctttg tgcgggggga gcggctcggg gggtgcgtgc  240
gtgtgtgtgt gcgtggggag cgccgcgtgc ggctccgcgc tgcccggcgg ctgtgagcgc  300
tgcgggcgcg gcgcggggct ttgtgcgctc cgcagtgtgc gcgaggggag cgcggccggg  360
ggcggtgccc cgcggtgcgg ggggggctgc gaggggaaca aaggctgcgt gcggggtgtg  420
tgcgtggggg ggtgagcagg gggtgtgggc gcgtcggtcg ggctgcaacc ccccctgcac  480
ccccctcccc gagttgctga gcacggcccg gcttcgggtg cggggctccg tacggggcgt  540
ggcgcggggc tcgccgtgcc gggcgggggg tggcggcagg tgggggtgcc gggcggggcg  600
gggccgcctc gggccgggga gggctcgggg gaggggcgcg gcggcccccg gagcgccggc  660
ggctgtcgag gcgcggcgag ccgcagccat tgccttttat ggtaatcgtg cgagagggcg  720
cagggacttc ctttgtccca aatctgtgcg gagccgaaat ctgggaggcg ccgccgcacc  780
ccctctagcg ggcgcggggc gaagcggtgc ggcgccggca ggaaggaaat gggcggggag  840
ggccttcgtg cgtcgccgcg ccgccgtccc cttctccctc tccagcctcg gggctgtccg  900
cggggggacg gctgccttcg gggggacgg ggcagggcgg ggttcggctt ctggcgtgtg  960
accggcggct ctagagcctc tgctaaccat gttcatgcct tcttcttttt cctacag     1017

SEQ ID NO: 5            moltype = DNA  length = 1572
FEATURE                 Location/Qualifiers
source                  1..1572
```

```
                        mol_type = other DNA
                        organism = synthetic construct
SEQUENCE: 5
gctggcctgt ggctgggcct ggtgtggcag aagctgttgc tgtggggggc tgcctctgcc  60
ctgagcctgg ctggggctag cctggtgttg agcctgctgc agagagtggc tagctatgct  120
agaaagtggc agcagatgag acccatcccc acagtggcaa gagcctaccc tctggtgggc  180
catgccctgc tgatgaagcc tgatggcaga gagttctttc agcagatcat agagtacaca  240
gaggagtaca gacacatgcc cctgctgaaa ctgtgggtgg gccctgtgcc catggtggct  300
ctgtacaatg ctgagaatgt ggaggtgatt ctgacaagca gcaagcagat tgacaagagc  360
tccatgtaca agttcctgga gccctggctg ggcctgggac tgctgacaag cactggcaac  420
aagtggagaa gcagaagaaa gatgctgacc cccaccttcc acttcaccat cctggaggac  480
ttcctggaca ttatgaatga gcaagccaac atcctggtga aaaagctgga aaagcacatc  540
aaccaagagg ccttcaactg cttcttctac atcaccctgt gtgccctgga catcatctgt  600
gagacagcca tgggcaagaa catcggggcc cagagcaatg atgactctga gtatgtgaga  660
gctgtgtaca gaatgtctga gatgatcttc agaagaatca agatgccctg gctgtggctg  720
gacctgtggt acctgatgtt caaggagggc tgggagcaca aaaagagcct gcagatcctg  780
cacaccttca ccaactctgt gatcgccgag agagccaatg agatgaatgc caatgaggac  840
tgcagagggg atggcagagg ctctgcccct agcaagaaca agagaagagc cttcctggac  900
ctgttgctgt ctgtgaccga cgatgagggc aacagactga gccatgagga catcagagaa  960
gaggtggaca catttatgtt tgagggccat gacaccacag ctgctgccat aaactggagc  1020
ctgtacctgc tgggcagcaa ccctgaggtg cagaagaagg tggaccatga gctggatgat  1080
gtgtttggca agtctgacag acctgccaca gtggaggacc tgaagaagct gagatacctg  1140
gagtgtgtga tcaaggagac cctgagactg ttcccctctg tgcccctgtt tgctagatct  1200
gtgtctgagg actgtgaggt ggctggctat agagtgctga agggcacaga ggctgtgatc  1260
atcccctatg ccctgcacag agaccctaga tacttcccca accctgagga gtttcagcct  1320
gagagattct tccctgagaa tgcccaaggc agacacccct atgcctatgt gccattctct  1380
gctggcccaa gaaactgcat tgggcagaag tttgctgtga tggaggagaa gaccatcctg  1440
agctgcatct tgagacactt ctggattgag agcaatcaga agagagagga gctgggcctg  1500
gaggggcagc tgatactgag accaagcaat ggcatctgga tcaagctgaa gagaagaaat  1560
gctgatgaga ga                                                  1572

SEQ ID NO: 6            moltype = DNA  length = 1572
FEATURE                 Location/Qualifiers
source                  1..1572
                        mol_type = other DNA
                        organism = synthetic construct
SEQUENCE: 6
gctggcctgt ggctgggcct ggtgtggcag aagctgctgc tgtggggagc tgcctctgcc  60
ctgtctctgg ctggagccag cctggtgctg agcctgctgc agagagtggc cagctatgcc  120
aggaaatggc aacagatgag acctatcccc acagtggcca gagcctaccc cctggttggc  180
catgccctgc tgatgaagcc tgatggcaga gagttcttcc agcagatcat tgagtacaca  240
gaagagtaca gacacatgcc tctgctgaag ctgtgggtgg gccctgtgcc catggtggcc  300
ctgtacaatg cagagaatgt ggaagtgatc ctgaccagca gcaagcagat agacaagtcc  360
agcatgtaca agttcctgga accttggctg ggcctgggcc tgctcacctc cacaggcaac  420
aagtggagaa gcagaaggaa gatgctgacc ccaaccttcc acttcaccat cctggaggac  480
tttctggaca tcatgaatga gcaggccaac atcctggtca aaaaactgga aaagcacatc  540
aaccaggaag ccttcaactg cttcttctac atcaccctgt gtgccctgga catcatctgc  600
gagacagcca tgggcaagaa catcggagcc cagagcaatg atgactctga atatgtcagg  660
gcagtgtaca gaatgtctga gatgatcttc cggcggatca agatgccttg gctgtggctg  720
gacctgtggt acctgatgtt caaagagggc tgggagcaca agaagagcct gcagatcctg  780
cacaccttca ccaacagcgt gattgctgag cgggccaatg aaatgaacgc caatgaggac  840
tgcagaggag atggcagagg ctctgccccc agcaagaaca agagaagagc cttcctggac  900
ctgctgctgt ccgtgacaga tgatgagggc aacagactga gccacgagga catcagagag  960
gaagtggaca cctttatgtt tgaaggccat gacaccacag ctgctgccat caactggagc  1020
ctgtacctcc tgggcagcaa ccctgaggtg cagaagaagg tggaccatga gctggatgat  1080
gtgtttggca agtctgacag acctgccaca gtggaagacc tgaagaaact caggtacctg  1140
gaatgtgtga tcaaagagac cctgagactg ttcccaagtg tgcctctgtt tgccagatct  1200
gtctctgagg actgtgaagt ggctggctac agagtgctga agggcacaga ggcagttatc  1260
atcccctatg ccctgcacag agaccccaga tacttcccca accctgaaga gttccagcct  1320
gagagattct tcccagagaa tgcccagggc agacaccctt atgcctatgt gcccttctca  1380
gctggaccta gaaactgcat aggccaaaag tttgcagtga tggaagagaa gaccatcctg  1440
agctgcatcc tgaggcactt ctggattgag agcaaccaga agagagagga actgggcctg  1500
gaaggacagc tgatcctgag gcctagcaat ggcatctgga tcaagctgaa aagaagaaat  1560
gctgatgaga gg                                                  1572

SEQ ID NO: 7            moltype = DNA  length = 1572
FEATURE                 Location/Qualifiers
source                  1..1572
                        mol_type = other DNA
                        organism = synthetic construct
SEQUENCE: 7
gctggcctgt ggctgggcct ggtgtggcag aaactgctgc tgtggggagc tgcctctgcc  60
ctgtctctgg ctggagcctc ccttgtcctg tccctcctgc aaagagttgc cagctatgcc  120
agaaagtggc agcagatgag acccatcccc acagtggcca gggcctaccc actggtgggc  180
catgccctgc tgatgaagcc tgatggcaga gaattctttc agcagatcat agagtacaca  240
gaggagtaca gacacatgcc tctgctgaag ctgtgggtgg gccctgtgcc tatggtggcc  300
ctgtacaatg ctgagaatgt ggaagtgatc ctgaccagca gcaagcagat tgacaagagc  360
agcatgtaca agttcctgga gccttggctg ggcctgggcc tgctgaccag cacaggcaac  420
aagtggagaa gcaggagaaa gatgctgacc cccaccttcc acttcaccat cctggaagac  480
```

-continued

```
ttcctggaca tcatgaatga gcaggccaac atcctggtga aaaagctgga aaaacacatc  540
aaccaggaag ccttcaactg cttcttctac attaccctgt gtgccctgga catcatctgc  600
gagacagcca tgggaaaaaa catcggagct cagagcaatg atgacagcga gtatgtgaga  660
gcagtgtacc ggatgagcga aatgatcttc agacggatca agatgccctg gctgtggctg  720
gacctgtggt acctcatgtt taaggagggc tgggaacaca agaagagcct gcagatcctg  780
cacaccttca caaacagtgt gatcgctgaa agggccaacg agatgaatgc caatgaggat  840
tgcagaggcg atggccgcgg ctccgcccct agcaagaaca agagaagagc cttcctggac  900
ctgctgctgt ctgtcaccga tgacgagggc aaccggctgt ctcatgagga catcagagaa  960
gaggtggaca ccttcatgtt tgagggccac gacaccacag ccgccgccat caactggagc  1020
ctgtacctgc ttggcagcaa ccctgaggtg caaaagaagg tggaccatga gctggatgat  1080
gtttttggca aatctgacag acctgccaca gtggaggacc tgaagaaact gagatacctg  1140
gagtgtgtga tcaaggaaac cctgagactc ttccctagtg tgcctctgtt tgccagatct  1200
gtctcagagg actgtgaggt ggctggctac agagtgctga agggcacaga agcagtgatc  1260
atcccctatg ccctgcacag agaccccaga tacttcccca accctgagga attccagcca  1320
gagaggttct tccctgagaa tgcccaggga agacacccat atgcctatgt gcctttctct  1380
gctggcccca gaaactgcat tggacagaag tttgctgtga tggaggaaaa gaccatcctg  1440
agctgcatcc tgagacactt ctggatagaa agcaaccaga agagggaaga gctgggcctg  1500
gaaggccagc tgatcctgag gcctagcaat ggcatctgga tcaaactgaa gagaagaaat  1560
gcagatgaga ga                                                      1572

SEQ ID NO: 8            moltype = DNA  length = 1572
FEATURE                 Location/Qualifiers
source                  1..1572
                        mol_type = other DNA
                        organism = synthetic construct
SEQUENCE: 8
gctggcctgt ggctgggcct ggtgtggcag aagctgctgc tgtggggagc tgcctctgcc  60
ctgtccctgg ctggagcctc tctggtgctg agcctgctgc agagagtggc cagctatgcc  120
aggaaatggc aacagatgag acccatccca acagtggcca gagcctaccc cctggttggc  180
catgccctgc tgatgaagcc tgatggcaga gagttcttcc agcagatcat tgagtacaca  240
gaggaataca gacacatgcc tctgctgaag ctgtgggtgg gccctgtgcc catggtggcc  300
ctgtacaatg cagagaatgt ggaagtgatc ctgacctcca gcaagcagat agacaagagc  360
agcatgtaca agttcctgga accttggctg ggccttggcc tgctcaccag cacaggcaac  420
aagtggagaa gcagaaggaa gatgctgacc cctaccttcc acttcaccat cctggaggac  480
tttctggaca tcatgaatga gcaggccaac atcctggtca aaaagctgga aaagcacatc  540
aaccaggagg ccttcaactg cttcttctac atcaccctgt gtgccctgga catcatctgc  600
gagacagcca tgggcaaaaa catcggagcc cagagcaatg atgactctga gtatgtgcgg  660
gctgtgtacc ggatgagcga aatgatcttc agacggatca agatgccctg gctgtggctg  720
gacctctggt acctgatgtt caaagaaggc tgggagcaca agaagagcct gcagatcctg  780
cacaccttca ccaacagcgt gattgcagaa agagccaatg agatgaatgc caacgaggac  840
tgcagaggag atggcagagg ctctgcccct agcaagaaca agagaagggc ctttctggac  900
ctgctgctgt ctgtcacaga tgatgagggc aacagactga gccacgagga catcagagag  960
gaagtggaca ccttcatgtt tgaaggccat gacaccacag ctgctgccat caactggtcc  1020
ctgtacctgc tgggcagcaa ccctgaggtg cagaagaagg tggaccatga gctggatgat  1080
gtgtttggca agtctgacag acctgccaca gtggaagacc tgaaaaagct gagatacctg  1140
gaatgtgtga tcaaagagac cctgagactg ttcccttctg tgcctctgtt tgccagaagt  1200
gtttctgagg actgtgaagt ggctggctac agagtgctga agggcacaga ggcagtcatc  1260
atcccctatg ccctgcacag agaccccagg tacttcccca accctgagga gttccagcct  1320
gaaagattct tcccagagaa tgcccagggc agacacccat atgcctatgt gcccttctca  1380
gctggaccta gaaactgcat aggacaaaag tttgcagtga tggaagagaa gaccatcctg  1440
agctgcatcc tgaggcactt ctggattgag agcaaccaga aaagagagga actgggcctg  1500
gaaggccagc tgatcctcag gcctagcaat ggcatctgga tcaagctgaa gagaaggaat  1560
gctgatgaga ga                                                      1572

SEQ ID NO: 9            moltype = DNA  length = 1572
FEATURE                 Location/Qualifiers
source                  1..1572
                        mol_type = other DNA
                        organism = synthetic construct
SEQUENCE: 9
gcggggctct ggctggggct cgtgtggcag aagctgctgc tgtggggcgc ggcgagtgcc  60
ctttccctgg ccggcgccag tctggtcctg agcctgctgc agagggtggc gagctacgcg  120
cggaaatggc agcagatgcg gcccatcccc acggtggccc gcgcctaccc actggtgggc  180
cacgcgctgc tgatgaagcc ggacgggcga gaatttttc agcagatcat tgagtacaca  240
gaggaatacc gccacatgcc gctgctgaag ctctgggtcg ggccagtgcc catggtggcc  300
ctttataatg cagaaaatgt ggaggtaatt ttaactagtt caaagcaaat tgacaaatcc  360
tctatgtaca agtttttaga accatggctt ggcctaggac ttcttacaag tactggaaac  420
aaatggcgct ccaggagaaa gatgttaaca cccactttcc attttaccat tctggaagat  480
ttcttagata tcatgaatga acaagcaaat atattggtta agaaacttga aaaacacatt  540
aaccaagaag catttaactg cttttttac atcactcttt gtgccttaga tatcatctgt  600
gaaacagcta tggggaagaa tattggtgct caaagtaatg atgattccga gtatgtccgt  660
gcagtttata gaatgagtga gatgatattt cgaagaataa agatgccctg gctttggctt  720
gatctctggt accttatgtt taaagaagga tgggaacaca aaaagagcct tcagatccta  780
catactttta ccaacagtgt catcgctgaa cgggccaatg aaatgaacgc caatgaagac  840
tgtagaggtg atggcagggg ctctgccccc tccaaaaata aacgcagggc ctttcttgac  900
ttgcttttaa gtgtgactga tgacgaaggg aacaggctaa gtcatgaaga tattcgagaa  960
gaagttgaca ccttcatgtt tgaggggcac gatacaactg cagctgcaat aaactggtcc  1020
ttatacctgt tgggttctaa cccagaagtc cagaaaaaag tggatcatga attggatgac  1080
gtgtttggga agtctgaccg tcccgctaca gtagaagacc tgaagaaact tcggtatctg  1140
```

-continued

```
gaatgtgtta ttaaggagac ccttcgcctt tttccttctg ttcctttatt tgcccgtagt  1200
gttagtgaag attgtgaagt ggcaggttac agagttctaa aaggcactga agccgtcatc  1260
attccctatg cattgcacag agatccgaga tacttcccca accccgagga gttccagcct  1320
gagcggttct tccccgagaa tgcacaaggg cgccatccat atgcctacgt gcccttctct  1380
gctggcccca ggaactgtat aggtcaaaag tttgctgtga tggaagaaaa gaccattctt  1440
tcgtgcatcc tgaggcactt ttggatagaa tccaaccaga aaagagaaga gcttggtcta  1500
gaaggacagt tgattcttcg tccaagtaat ggcatctgga tcaagttgaa gaggagaaat  1560
gcagatgaac gc                                                      1572

SEQ ID NO: 10          moltype = DNA  length = 225
FEATURE                Location/Qualifiers
source                 1..225
                       mol_type = other DNA
                       organism = synthetic construct
SEQUENCE: 10
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
gggaagacaa tagcaggcat gctggggatg cggtgggctc tatgg                 225

SEQ ID NO: 11          moltype = DNA  length = 145
FEATURE                Location/Qualifiers
source                 1..145
                       mol_type = other DNA
                       organism = synthetic construct
SEQUENCE: 11
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag agagggagtg gccaa                                       145

SEQ ID NO: 12          moltype = DNA  length = 3961
FEATURE                Location/Qualifiers
source                 1..3961
                       mol_type = other DNA
                       organism = synthetic construct
SEQUENCE: 12
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctctcga ggagcttggc ccattgcata cgttgtatcc  180
atatcataat atgtacattt atattggctc atgtccaaca ttaccgccat gttactagtg  240
tcgacattga ttattgacta gttattaata gtaatcaatt acggggtcat tagttcatag  300
cccatatatg gagttccgcg ttacataact tacggtaaat ggcccgcctg gctgaccgcc  360
caacgacccc cgcccattga cgtcaataat gacgtatgtt cccatagtaa cgccaatagg  420
gactttccat tgacgtcaat gggtggagta tttacggtaa actgcccact tggcagtaca  480
tcaagtgtat catatgccaa gtacgccccc tattgacgtc aatgacggta aatggcccgc  540
ctggcattat gcccagtaca tgaccttatg ggactttcct acttggcagt acatctacgt  600
attagtcatc gctattacca tggtcgaggt gagccccacg ttctgcttca ctctccccat  660
ctcccccccc tccccacccc caattttgta tttatttatt ttttaattat tttgtgcagc  720
gatgggggcg gggggggggg ggggcgcgc gccaggcggg gcggggcggg gcgaggggcg  780
gggcggggcg aggcggagag gtgcggcggc agccaatcag agcggcgcgc tccgaaagtt  840
tccttttatg gcgaggcggc ggcggcggcg gccctataaa aagcgaagcg cgcggcgggc  900
gggagtcgct gcgcgctgcc ttcgccccgt gccccgctcc gccgccgcct cgcgccgccc  960
gccccggctc tgactgaccg cgttactccc acaggtgagc gggcgggacg gcccttctcc  1020
tccgggctgt aattagcgct tggtttaatg acggcttgtt tcttttctgt ggctgcgtga  1080
aagccttgag gggctccggg agggcccttt gtgcgggggg agcggctcgg ggggtgcgtg  1140
cgtgtgtgtg tgcgtgggga gcgccgcgtg cggctccgcg ctgcccggcg gctgtgagcg  1200
ctgcgggcgc ggcgcggggc tttgtgcgct ccgcagtgtg cgcgagggga gcgcggccgg  1260
gggcggtgcc ccgcggtgcg gggggggctg cgaggggaac aaaggctgcg tgcggggtgt  1320
gtgcgtgggg gggtgagcag ggggtgtggg cgcgtcggtc gggctgcaac ccccccctgca  1380
ccccctccc cgagttgctg agcacggccc ggcttcgggt gcggggctcc gtacggggcg  1440
tggcgcgggg ctcgccgtgc cgggcggggg gtggcggcag gtgggggtgc cgggcggggc  1500
ggggccgcct cgggccgggg agggctcggg ggaggggcgc ggcggccccc ggagcgccgg  1560
cggctgtcga ggcgcggcga gccgcagcca ttgcctttta tggtaatcgt gcgagagggc  1620
gcagggactt cctttgtccc aaatctgtgc ggagccgaaa tctgggaggc gccgccgcac  1680
cccctctagc gggcgcgggg cgaagcggtg cggcgccggc aggaaggaaa tgggcgggga  1740
gggccttcgt gcgtcgccgc gccgccgtcc ccttctccct ctccagcctc ggggctgtcc  1800
gcggggggac ggctgccttc ggggggggacg ggcagggcg gggttcggct tctggcgtgt  1860
gaccggcggc tctagagcct ctgctaacca tgttcatgcc ttcttctttt tcctacagct  1920
cctgggcaac gtgctggtta ttgtgctgtc tcatcatttt ggcaaagaat tcggcgcgcc  1980
gccaccatgg ctggcctgtg gctgggcctg gtgtggcaga agctgctgct gtggggagct  2040
gcctctgccc tgtccctggc tggagcctct ctggtgctga gcctgctgca gagagtggcc  2100
agctatgcca ggaaatggca acagatgaga cccatcccaa cagtggccag agcctacccc  2160
ctggttggcc atgccctgct gatgaagcct gatggcagag agttcttcca gcagatcatt  2220
gagtacacag aggaatacag acacatgcct ctgctgaagc tgtgggtggg ccctgtgccc  2280
atggtggccc tgtacaatgc agagaatgtg gaagtgatcc tgacctccag caagcagata  2340
gacaagagca gcatgtacaa gttcctggaa ccttggctgg gccttggcct gctcaccagc  2400
acaggcaaca agtggagaag cagaaggaag atgctgaccc ctaccttcca cttcaccatc  2460
ctggaggact ttctggacat catgaatgag caggccaaca tcctggtcaa aaagctggaa  2520
aagcacatca accaggaggc cttcaactgc ttcttctaca tcaccctgtg tgccctggac  2580
```

-continued

```
atcatctgcg agacagccat gggcaaaaac atcggagccc agagcaatga tgactctgag  2640
tatgtgcggg ctgtgtaccg gatgagcgaa atgatcttca gacggatcaa gatgccctgg  2700
ctgtggctgg acctctggta cctgatgttc aaagaaggct gggagcacaa gaagagcctg  2760
cagatcctgc acaccttcac caacagcgtg attgcagaaa gagccaatga gatgaatgcc  2820
aacgaggact gcagaggaga tggcagaggc tctgccccta gcaagaacaa gagaagggcc  2880
tttctggacc tgctgctgtc tgtcacagat gatgagggca acagactgag ccacgaggac  2940
atcagagagg aagtggacac cttcatgttt gaaggccatg acaccacagc tgctgccatc  3000
aactggtccc tgtacctgct gggcagcaac cctgaggtgc agaagaaggt ggaccatgag  3060
ctggatgatg tgtttggcaa gtctgacaga cctgccacag tggaagacct gaaaaagctg  3120
agatacctgg aatgtgtgat caaagagacc ctgagactgt tcccttctgt gcctctgttt  3180
gccagaagtg tttctgagga ctgtgaagtg gctggctaca gagtgctgaa gggcacagag  3240
gcagtcatca tcccctatgc cctgcacaga gaccccaggt acttccccaa ccctgaggag  3300
ttccagcctg aaagattctt cccagagaat gcccagggca gacacccata tgcctatgtg  3360
cccttctcag ctggacctag aaactgcata ggacaaaagt ttgcagtgat ggaagagaag  3420
accatcctga gctgcatcct gaggcacttc tggattgaga gcaaccagaa aagagaggaa  3480
ctgggcctgg aaggccagct gatcctcagg cctagcaatg gcatctggat caagctgaag  3540
agaaggaatg ctgatgagag ataaagatct gcctcgactg tgccttctag ttgccagcca  3600
tctgttgttt gcccctcccc cgtgccttcc ttgaccctgg aaggtgccac tcccactgtc  3660
ctttcctaat aaaatgagga aattgcatcg cattgtctga gtaggtgtca ttctattctg  3720
gggggtgggg tggggcagga cagcaagggg gaggattggg aagacaatag caggcatgct  3780
ggggatgcgg tgggctctat ggatccccta actacaagga acccctagtg atggagttgg  3840
ccactccctc tctgcgcgct cgctcgctca ctgaggccgg gcgaccaaag gtcgcccgac  3900
gcccgggctt tgcccgggcg gcctcagtga gcgagcgagc gcgcagagag ggagtggcca  3960
a                                                                  3961
```

```
SEQ ID NO: 13           moltype = DNA  length = 3961
FEATURE                 Location/Qualifiers
source                  1..3961
                        mol_type = other DNA
                        organism = synthetic construct
SEQUENCE: 13
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctctcga ggagcttggc ccattgcata cgttgtatcc  180
atatcataat atgtacattt atattggctc atgtccaaca ttaccgccat gttactagtg  240
tcgacattga ttattgacta gttattaata gtaatcaatt acggggtcat tagttcatag  300
cccatatatg gagttccgcg ttacataact tacggtaaat ggcccgcctg gctgaccgcc  360
caacgacccc cgcccattga cgtcaataat gacgtatgtt cccatagtaa cgccaatagg  420
gactttccat tgacgtcaat gggtggagta tttacggtaa actgcccact tggcagtaca  480
tcaagtgtat catatgccaa gtacgccccc tattgacgtc aatgacggta aatggcccgc  540
ctggcattat gcccagtaca tgaccttatg ggactttcct acttggcagt acatctacgt  600
attagtcatc gctattacca tggtcgaggt gagccccacg ttctgcttca ctctccccat  660
ctcccccccc tccccacccc caattttgta tttatttatt ttttaattat tttgtgcagc  720
gatgggggcg gggggggggg ggggcgcgc gccaggcggg gcggggcggg gcgaggggcg  780
gggcggggcg aggcggagag gtgcggcggc agccaatcag agcggcgcgc tccgaaagtt  840
tccttttatg gcgaggcggc ggcggcggcg gccctataaa aagcgaagcg cgcggcgggc  900
gggagtcgct gcgcgctgcc ttcgccccgt gccccgctcc gccgccgcct cgcgccgccc  960
gccccggctc tgactgaccg cgttactccc acaggtgagc gggcgggacg gcccttctcc  1020
tccgggctgt aattagcgct tggtttaatg acggcttgtt tctttctgt ggctgcgtga  1080
aagccttgag gggctccggg agggcccttt gtgcgggggg agcggctcgg ggggtgcgtg  1140
cgtgtgtgtg tgcgtgggga gcgccgcgtg cggctccgcg ctgcccggcg gctgtgagcg  1200
ctgcgggcgc ggcgcggggc tttgtgcgct ccgcagtgtg cgcgagggga gcgcggccgg  1260
gggcggtgcc ccgcggtgcg gggggggctg cgaggggaac aaaggctgcg tgcggggtgt  1320
gtgcgtgggg gggtgagcag ggggtgtggg cgcgtcggtc gggctgcaac cccccctgca  1380
ccccctccc cgagttgctg agcacggccc ggcttcgggt gcggggctcc gtacggggcg  1440
tggcgcgggg ctcgccgtgc cgggcggggg gtggcggcag gtgggggtgc cgggcggggc  1500
ggggccgcct cgggccgggg agggctcggg ggaggggcgc ggcggccccc ggagcgccgg  1560
cggctgtcga ggcgcggcga gccgcagcca ttgcctttta tggtaatcgt gcgagagggc  1620
gcagggactt cctttgtccc aaatctgtgc ggagccgaaa tctgggaggc gccgccgcac  1680
cccctctagc gggcgcgggg cgaagcggtg cggcgccggc aggaaggaaa tgggcgggga  1740
gggccttcgt gcgtcgccgc gccgccgtcc ccttctccct ctccagcctc ggggctgtcc  1800
gcggggggac ggctgccttc ggggggggacg gggcagggcg gggttcggct tctggcgtgt  1860
gaccggcggc tctagagcct ctgctaacca tgttcatgcc ttcttctttt tcctacagct  1920
cctgggcaac gtgctggtta ttgtgctgtc tcatcatttt ggcaaagaat tcggcgcgcc  1980
gccaccatgg ctggcctgtg gctgggcctg gtgtggcaga agctgctgct gtggggagct  2040
gcctctgccc tgtctctggc tggagccagc ctggtgctga gcctgctgca gagagtggcc  2100
agctatgcca ggaaatggca acagatgaga cctatcccca cagtggccag agcctacccc  2160
ctggttggcc atgccctgct gatgaagcct gatggcagag agttcttcca gcagatcatt  2220
gagtacacag aagagtacag acacatgcct ctgctgaagc tgtgggtggg ccctgtgccc  2280
atggtggccc tgtacaatgc agagaatgtg gaagtgatcc tgaccagcag caagcagata  2340
gacaagtcca gcatgtacaa gttcctggaa ccttggctgg gcctgggcct gctcacctcc  2400
acaggcaaca agtggagaag cagaaggaag atgctgaccc caaccttcca cttcaccatc  2460
ctggaggact ttctggacat catgaatgag caggccaaca tcctggtcaa aaaactggaa  2520
aagcacatca accaggaagc cttcaactgc ttcttctaca tcaccctgtg tgccctggac  2580
atcatctgcg agacagccat gggcaagaac atcggagccc agagcaatga tgactctgaa  2640
tatgtcaggg cagtgtacag aatgtctgag atgatcttcc ggcggatcaa gatgccttgg  2700
ctgtggctgg acctgtggta cctgatgttc aaagagggct gggagcacaa gaagagcctg  2760
cagatcctgc acaccttcac caacagcgtg attgctgagc gggccaatga aatgaacgcc  2820
aatgaggact gcagaggaga tggcagaggc tctgccccca gcaagaacaa gagaagagcc  2880
```

-continued

```
ttcctggacc tgctgctgtc cgtgacagat gatgagggca acagactgag ccacgaggac  2940
atcagagagg aagtggacac ctttatgttt gaaggccatg acaccacagc tgctgccatc  3000
aactggagcc tgtacctcct gggcagcaac cctgaggtgc agaagaaggt ggaccatgag  3060
ctggatgatg tgtttggcaa gtctgacaga cctgccacag tggaagacct gaagaaactc  3120
aggtacctgg aatgtgtgat caaagagacc ctgagactgt tcccaagtgt gcctctgttt  3180
gccagatctg tctctgagga ctgtgaagtg gctggctaca gagtgctgaa gggcacagag  3240
gcagttatca tcccctatgc cctgcacaga gaccccagat acttccccaa ccctgaagag  3300
ttccagcctg agagattctt cccagagaat gcccagggca gacaccctta tgcctatgtg  3360
cccttctcag ctggacctag aaactgcata ggccaaaagt ttgcagtgat ggaagagaag  3420
accatcctga gctgcatcct gaggcacttc tggattgaga gcaaccagaa gagagaggaa  3480
ctgggcctgg aaggacagct gatcctgagg cctagcaatg gcatctggat caagctgaaa  3540
agaagaaatg ctgatgagag gtaaagatct gcctcgactg tgccttctag ttgccagcca  3600
tctgttgttt gcccctcccc cgtgccttcc ttgaccctgg aaggtgccac tcccactgtc  3660
ctttcctaat aaaatgagga aattgcatcg cattgtctga gtaggtgtca ttctattctg  3720
gggggtgggg tggggcagga cagcaagggg gaggattggg aagacaatag caggcatgct  3780
ggggatgcgg tgggctctat ggatccccta actacaagga acccctagtg atggagttgg  3840
ccactccctc tctgcgcgct cgctcgctca ctgaggccgg gcgaccaaag gtcgcccgac  3900
gcccgggctt tgcccgggcg gcctcagtga gcgagcgagc gcgcagagag ggagtggcca  3960
a                                                                 3961

SEQ ID NO: 14          moltype = DNA  length = 3961
FEATURE                Location/Qualifiers
source                 1..3961
                       mol_type = other DNA
                       organism = synthetic construct
SEQUENCE: 14
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctctcga ggagcttggc ccattgcata cgttgtatcc  180
atatcataat atgtacattt atattggctc atgtccaaca ttaccgccat gttactagtg  240
tcgacattga ttattgacta gttattaata gtaatcaatt acggggtcat tagttcatag  300
cccatatatg gagttccgcg ttacataact tacggtaaat ggcccgcctg gctgaccgcc  360
caacgacccc cgcccattga cgtcaataat gacgtatgtt cccatagtaa cgccaatagg  420
gactttccat tgacgtcaat gggtggagta tttacggtaa actgcccact tggcagtaca  480
tcaagtgtat catatgccaa gtacgccccc tattgacgtc aatgacggta aatggcccgc  540
ctggcattat gcccagtaca tgaccttatg ggactttcct acttggcagt acatctacgt  600
attagtcatc gctattacca tggtcgaggt gagccccacg ttctgcttca ctctccccat  660
ctcccccccc tccccacccc caattttgta tttatttatt ttttaattat tttgtgcagc  720
gatgggggcg gggggggggg gggggcgcgc gccaggcggg gcggggcggg gcgaggggcg  780
gggcggggcg aggcggagag gtgcggcggc agccaatcag agcggcgcgc tccgaaagtt  840
tccttttatg gcgaggcggc ggcggcggcg gccctataaa aagcgaagcg cgcggcgggc  900
gggagtcgct gcgcgctgcc ttcgccccgt gccccgctcc gccgccgcct cgcgccgccc  960
gccccggctc tgactgaccg cgttactccc acaggtgagc gggcgggacg gcccttctcc  1020
tccgggctgt aattagcgct tggtttaatg acggcttgtt tcttttctgt ggctgcgtga  1080
aagccttgag gggctccggg agggcccttt gtgcgggggg agcggctcgg ggggtgcgtg  1140
cgtgtgtgtg tgcgtgggga gcgccgcgtg cggctccgcg ctgcccggcg gctgtgagcg  1200
ctgcgggcgc ggcgcggggc tttgtgcgct ccgcagtgtg cgcgagggga gcgcggccgg  1260
gggcggtgcc ccgcggtgcg gggggggctg cgaggggaac aaaggctgcg tgcggggtgt  1320
gtgcgtgggg gggtgagcag ggggtgtggg cgcgtcggtc gggctgcaac cccccctgca  1380
cccccctccc cgagttgctg agcacggccc ggcttcgggt gcggggctcc gtacggggcg  1440
tggcgcgggg ctcgccgtgc cgggcggggg gtggcggcag gtgggggtgc cgggcggggc  1500
ggggccgcct cgggccgggg agggctcggg ggaggggcgc ggcggccccc ggagcgccgg  1560
cggctgtcga ggcgcggcga gccgcagcca ttgcctttta tggtaatcgt gcgagagggc  1620
gcagggactt cctttgtccc aaatctgtgc ggagccgaaa tctgggaggc gccgccgcac  1680
cccctctagc gggcgcgggg cgaagcggtg cggcgccggc aggaaggaaa tgggcgggga  1740
gggccttcgt gcgtcgccgc gccgccgtcc ccttctccct ctccagcctc ggggctgtcc  1800
gcggggggac ggctgccttc gggggggacg ggcagggcgg gggttcggct tctggcgtgt  1860
gaccggcggc tctagagcct ctgctaacca tgttcatgcc ttcttctttt tcctacagct  1920
cctgggcaac gtgctggtta ttgtgctgtc tcatcatttt ggcaaagaat tcggcgcgcc  1980
gccaccatgg ctggcctgtg gctgggcctg gtgtggcaga aactgctgct gtggggagct  2040
gcctctgccc tgtctctggc tggagcctcc cttgtcctgt ccctcctgca aagagttgcc  2100
agctatgcca gaaagtggca gcagatgaga cccatcccca cagtggccag ggcctaccca  2160
ctggtgggcc atgccctgct gatgaagcct gatggcagag aattctttca gcagatcata  2220
gagtacacag aggagtacag acacatgcct ctgctgaagc tgtgggtggg ccctgtgcct  2280
atggtggccc tgtacaatgc tgagaatgtg gaagtgatcc tgaccagcag caagcagatt  2340
gacaagagca gcatgtacaa gttcctggag ccttggctgg gcctgggcct gctgaccagc  2400
acaggcaaca agtggagaag caggagaaag atgctgaccc ccaccttcca cttcaccatc  2460
ctggaagact tcctggacat catgaatgag caggccaaca tcctggtgaa aaagctggaa  2520
aaacacatca accaggaagc cttcaactgc ttcttctaca ttaccctgtg tgccctggac  2580
atcatctgcg agacagccat gggaaaaaac atcggagctc agagcaatga tgacagcgag  2640
tatgtgagag cagtgtaccg gatgagcgaa atgatcttca gacggatcaa gatgccctgg  2700
ctgtggctgg acctgtggta cctcatgttt aaggagggct gggaacacaa gaagagcctg  2760
cagatcctgc acaccttcac aaacagtgtg atcgctgaaa gggccaacga gatgaatgcc  2820
aatgaggatt gcagaggcga tggccgcggc tccgccccta gcaagaacaa gagaagagcc  2880
ttcctggacc tgctgctgtc tgtcaccgat gacgagggca accggctgtc tcatgaggac  2940
atcagagaag aggtggacac cttcatgttt gagggccacg acaccacagc cgccgccatc  3000
aactggagcc tgtacctgct tggcagcaac cctgaggtgc aaaagaaggt ggaccatgag  3060
ctggatgatg tttttggcaa atctgacaga cctgccacag tggaggacct gaagaaactg  3120
agatacctgg agtgtgtgat caaggaaacc ctgagactct tccctagtgt gcctctgttt  3180
```

-continued

```
gccagatctg tctcagagga ctgtgaggtg gctggctaca gagtgctgaa gggcacagaa  3240
gcagtgatca tcccctatgc cctgcacaga gaccccagat acttccccaa ccctgaggaa  3300
ttccagccag agaggttctt ccctgagaat gcccagggaa gacacccata tgcctatgtg  3360
cctttctctg ctggccccag aaactgcatt ggacagaagt ttgctgtgat ggaggaaaag  3420
accatcctga gctgcatcct gagacacttc tggatagaaa gcaaccagaa gagggaagag  3480
ctgggcctgg aaggccagct gatcctgagg cctagcaatg gcatctggat caaactgaag  3540
agaagaaatg cagatgagag ataaagatct gcctcgactg tgccttctag ttgccagcca  3600
tctgttgttt gcccctcccc cgtgccttcc ttgaccctgg aaggtgccac tcccactgtc  3660
ctttcctaat aaaatgagga aattgcatcg cattgtctga gtaggtgtca ttctattctg  3720
gggggtgggg tggggcagga cagcaagggg gaggattggg aagacaatag caggcatgct  3780
ggggatgcgg tgggctctat ggatccccta actacaagga acccctagtg atggagttgg  3840
ccactccctc tctgcgcgct cgctcgctca ctgaggccgg gcgaccaaag gtcgcccgac  3900
gcccgggctt tgcccgggcg gcctcagtga gcgagcgagc gcgcagagag ggagtggcca  3960
a                                                                   3961

SEQ ID NO: 15          moltype = DNA  length = 3961
FEATURE                Location/Qualifiers
source                 1..3961
                       mol_type = other DNA
                       organism = synthetic construct
SEQUENCE: 15
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctctcga ggagcttggc ccattgcata cgttgtatcc  180
atatcataat atgtacattt atattggctc atgtccaaca ttaccgccat gttactagtg  240
tcgacattga ttattgacta gttattaata gtaatcaatt acggggtcat tagttcatag  300
cccatatatg gagttccgcg ttacataact tacggtaaat ggcccgcctg gctgaccgcc  360
caacgacccc cgcccattga cgtcaataat gacgtatgtt cccatagtaa cgccaatagg  420
gactttccat tgacgtcaat gggtggagta tttacggtaa actgcccact tggcagtaca  480
tcaagtgtat catatgccaa gtacgccccc tattgacgtc aatgacggta aatggcccgc  540
ctggcattat gcccagtaca tgaccttatg ggactttcct acttggcagt acatctacgt  600
attagtcatc gctattacca tggtcgaggt gagccccacg ttctgcttca ctctccccat  660
ctcccccccc tccccacccc caattttgta tttatttatt ttttaattat tttgtgcagc  720
gatgggggcg gggggggggg ggggcgcgc gccaggcggg gcggggcggg gcgaggggcg  780
gggcggggcg aggcggagag gtgcggcggc agccaatcag agcggcgcgc tccgaaagtt  840
tccttttatg gcgaggcggc ggcggcggcg gccctataaa aagcgaagcg cgcggcgggc  900
gggagtcgct gcgcgctgcc ttcgccccgt gccccgctcc gccgccgcct cgcgccgccc  960
gccccggctc tgactgaccg cgttactccc acaggtgagc gggcgggacg gcccttctcc  1020
tccgggctgt aattagcgct tggtttaatg acggcttgtt tcttttctgt ggctgcgtga  1080
aagccttgag gggctccggg agggcccttt gtgcgggggg agcggctcgg ggggtgcgtg  1140
cgtgtgtgtg tgcgtgggga gcgccgcgtg cggctccgcg ctgcccggcg gctgtgagcg  1200
ctgcgggcgc ggcgcggggc tttgtgcgct ccgcagtgtg cgcgagggga gcgcggccgg  1260
gggcggtgcc ccgcggtgcg gggggggctg cgaggggaac aaaggctgcg tgcggggtgt  1320
gtgcgtgggg gggtgagcag ggggtgtggg cgcgtcggtc gggctgcaac cccccctgca  1380
cccccctccc cgagttgctg agcacggccc ggcttcgggt gcggggctcc gtacggggcg  1440
tggcgcgggg ctcgccgtgc cgggcggggg gtggcggcag gtgggggtgc cgggcggggc  1500
ggggccgcct cgggccgggg agggctcggg ggaggggcgc ggcggccccc ggagcgccgg  1560
cggctgtcga ggcgcggcga gccgcagcca ttgcctttta tggtaatcgt gcgagagggc  1620
gcagggactt cctttgtccc aaatctgtgc ggagccgaaa tctgggaggc gccgccgcac  1680
cccctctagc gggcgcgggg cgaagcggtg cggcgccggc aggaaggaaa tgggcgggga  1740
gggccttcgt gcgtcgccgc gccgccgtcc ccttctccct ctccagcctc ggggctgtcc  1800
gcggggggac ggctgccttc ggggggggacg gggcagggcg gggttcggct tctggcgtgt  1860
gaccggcggc tctagagcct ctgctaacca tgttcatgcc ttcttctttt tcctacagct  1920
cctgggcaac gtgctggtta ttgtgctgtc tcatcatttt ggcaaagaat tcggcgcgcc  1980
gccaccatgg ctggcctgtg gctgggcctg gtgtggcaga agctgttgct gtggggggct  2040
gcctctgccc tgagcctggc tggggctagc ctggtgttga gcctgctgca gagagtggct  2100
agctatgcta gaaagtggca gcagatgaga cccatcccca cagtggcaag agcctacct   2160
ctggtgggcc atgccctgct gatgaagcct gatggcagag agttctttca gcagatcata  2220
gagtacacag aggagtacag acacatgccc ctgctgaaac tgtgggtggg ccctgtgccc  2280
atggtggctc tgtacaatgc tgagaatgtg gaggtgattc tgacaagcag caagcagatt  2340
gacaagagct ccatgtacaa gttcctggag ccctggctgg gcctgggact gctgacaagc  2400
actggcaaca agtggagaag cagaagaaag atgctgaccc ccaccttcca cttcaccatc  2460
ctggaggact tcctggacat tatgaatgag caagccaaca tcctggtgaa aaagctggaa  2520
aagcacatca accaagaggc cttcaactgc ttcttctaca tcaccctgtg tgccctggac  2580
atcatctgtg agacagccat gggcaagaac atcggggccc agagcaatga tgactctgag  2640
tatgtgagag ctgtgtacag aatgtctgag atgatcttca gaagaatcaa gatgccctgg  2700
ctgtggctgg acctgtggta cctgatgttc aaggagggct gggagcacaa aaagagcctg  2760
cagatcctgc acaccttcac caactctgtg atcgccgaga gagccaatga gatgaatgcc  2820
aatgaggact gcagagggga tggcagaggc tctgccccta gcaagaacaa gagaagagcc  2880
ttcctggacc tgttgctgtc tgtgaccgac gatgagggca acagactgag ccatgaggac  2940
atcagagaag aggtggacac atttatgttt gagggccatg acaccacagc tgctgccata  3000
aactggagcc tgtacctgct gggcagcaac cctgaggtgc agaagaaggt ggaccatgag  3060
ctggatgatg tgtttggcaa gtctgacaga cctgccacag tggaggacct gaagaagctg  3120
agatacctgg agtgtgtgat caaggagacc ctgagactgt tcccctctgt gcccctgttt  3180
gctagatctg tgtctgagga ctgtgaggtg gctggctata gagtgctgaa gggcacagag  3240
gctgtgatca tcccctatgc cctgcacaga gaccctagat acttccccaa ccctgaggag  3300
tttcagcctg agagattctt ccctgagaat gcccaaggca gacaccccta tgcctatgtg  3360
ccattctctg ctggcccaag aaactgcatt gggcagaagt ttgctgtgat ggaggagaag  3420
accatcctga gctgcatctt gagacacttc tggattgaga gcaatcagaa gagagaggag  3480
```

-continued

```
ctgggcctgg aggggcagct gatactgaga ccaagcaatg gcatctggat caagctgaag  3540
agaagaaatg ctgatgagag ataaagatct gcctcgactg tgccttctag ttgccagcca  3600
tctgttgttt gcccctcccc cgtgccttcc ttgaccctgg aaggtgccac tcccactgtc  3660
ctttcctaat aaaatgagga aattgcatcg cattgtctga gtaggtgtca ttctattctg  3720
gggggtgggg tggggcagga cagcaagggg gaggattggg aagacaatag caggcatgct  3780
ggggatgcgg tgggctctat ggatccccta actacaagga acccctagtg atggagttgg  3840
ccactccctc tctgcgcgct cgctcgctca ctgaggccgg gcgaccaaag gtcgcccgac  3900
gcccgggctt tgcccgggcg gcctcagtga gcgagcgagc gcgcagagag ggagtggcca  3960
a                                                                  3961

SEQ ID NO: 16          moltype = DNA  length = 3961
FEATURE                Location/Qualifiers
source                 1..3961
                       mol_type = other DNA
                       organism = synthetic construct
SEQUENCE: 16
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctctcga ggagcttggc ccattgcata cgttgtatcc  180
atatcataat atgtacattt atattggctc atgtccaaca ttaccgccat gttactagtg  240
tcgacattga ttattgacta gttattaata gtaatcaatt acggggtcat tagttcatag  300
cccatatatg gagttccgcg ttacataact tacggtaaat ggcccgcctg gctgaccgcc  360
caacgacccc cgcccattga cgtcaataat gacgtatgtt cccatagtaa cgccaatagg  420
gactttccat tgacgtcaat gggtggagta tttacggtaa actgcccact tggcagtaca  480
tcaagtgtat catatgccaa gtacgccccc tattgacgtc aatgacggta aatggcccgc  540
ctggcattat gcccagtaca tgaccttatg ggactttcct acttggcagt acatctacgt  600
attagtcatc gctattacca tggtcgaggt gagccccacg ttctgcttca ctctccccat  660
ctcccccccc tccccacccc caattttgta tttatttatt ttttaattat tttgtgcagc  720
gatgggggcg gggggggggg ggggcgcgcg ccaggcgggg gcggggcggg gcgaggggcg  780
gggcggggcg aggcggagag gtgcggcggc agccaatcag agcggcgcgc tccgaaagtt  840
tccttttatg gcgaggcggc ggcggcggcg gccctataaa aagcgaagcg cgcggcgggc  900
gggagtcgct gcgcgctgcc ttcgccccgt gccccgctcc gccgccgcct cgcgccgccc  960
gccccggctc tgactgaccg cgttactccc acaggtgagc gggcgggacg gcccttctcc  1020
tccgggctgt aattagcgct tggtttaatg acggcttgtt tctttctgt ggctgcgtga  1080
aagccttgag gggctccggg agggcccttt gtgcgggggg agcggctcgg ggggtgcgtg  1140
cgtgtgtgtg tgcgtgggga gcgccgcgtg cggctccgcg ctgcccggcg gctgtgagcg  1200
ctgcgggcgc ggcgcggggc tttgtgcgct ccgcagtgtg cgcgagggga gcgcggccgg  1260
gggcggtgcc ccgcggtgcg gggggggctg cgaggggaac aaaggctgcg tgcggggtgt  1320
gtgcgtgggg gggtgagcag ggggtgtggg cgcgtcggtc gggctgcaac cccccctgca  1380
cccccctccc cgagttgctg agcacggccc ggcttcgggt gcggggctcc gtacggggcg  1440
tggcgcgggg ctcgccgtgc cgggcggggg gtggcggcag gtgggggtgc cgggcggggc  1500
ggggccgcct cgggccgggg agggctcggg ggaggggcgc ggcggccccc ggagcgccgg  1560
cggctgtcga ggcgcggcga gccgcagcca ttgcctttta tggtaatcgt gcgagagggc  1620
gcagggactt cctttgtccc aaatctgtgc ggagccgaaa tctgggaggc gccgccgcac  1680
cccctctagc gggcgcgggg cgaagcggtg cggcgccggc aggaaggaaa tgggcgggga  1740
gggccttcgt gcgtcgccgc gccgccgtcc ccttctccct ctccagcctc ggggctgtcc  1800
gcggggggac ggctgccttc ggggggggacg gggcagggcg gggttcggct tctggcgtgt  1860
gaccggcggc tctagagcct ctgctaacca tgttcatgcc ttcttctttt tcctacagct  1920
cctgggcaac gtgctggtta ttgtgctgtc tcatcatttt ggcaaagaat tcggcgcgcc  1980
gccaccatgg cggggctctg gctggggctc gtgtggcaga agctgctgct gtggggcgcg  2040
gcgagtgccc tttccctggc cggcgccagt ctggtcctga gcctgctgca gagggtggcg  2100
agctacgcgc ggaaatggca gcagatgcgg cccatcccca cggtggcccg cgcctaccca  2160
ctggtgggcc acgcgctgct gatgaagccg gacgggcgag aattttttca gcagatcatt  2220
gagtacacag aggaataccg ccacatgccg ctgctgaagc tctgggtcgg gccagtgccc  2280
atggtggccc tttataatgc agaaaatgtg gaggtaattt taactagttc aaagcaaatt  2340
gacaaatcct ctatgtacaa gtttttagaa ccatggcttg gcctaggact tcttacaagt  2400
actggaaaca aatggcgctc caggagaaag atgttaacac ccactttcca ttttaccatt  2460
ctggaagatt tcttagatat catgaatgaa caagcaaata tattggttaa gaaacttgaa  2520
aaacacatta accaagaagc atttaactgc ttttttaca tcactctttg tgccttagat  2580
atcatctgtg aaacagctat ggggaagaat attggtgctc aaagtaatga tgattccgag  2640
tatgtccgtg cagtttatag aatgagtgag atgatatttc gaagaataaa gatgccctgg  2700
ctttggcttg atctctggta ccttatgttt aaagaaggat gggaacacaa aaagagcctt  2760
cagatcctac atactttac caacagtgtc atcgctgaac gggccaatga aatgaacgcc  2820
aatgaagact gtagaggtga tggcaggggc tctgccccct ccaaaaataa acgcagggcc  2880
tttcttgact tgcttttaag tgtgactgat gacgaaggga acaggctaag tcatgaagat  2940
attcgagaag aagttgacac cttcatgttt gaggggcacg atacaactgc agctgcaata  3000
aactggtcct tatacctgtt gggttctaac ccagaagtcc agaaaaaagt ggatcatgaa  3060
ttggatgacg tgtttgggaa gtctgaccgt cccgctacag tagaagacct gaagaaactt  3120
cggtatctgg aatgtgttat taaggagacc cttcgccttt ttccttctgt tcctttattt  3180
gcccgtagtg ttagtgaaga ttgtgaagtg gcaggttaca gagttctaaa aggcactgaa  3240
gccgtcatca ttccctatgc attgcacaga gatccgagat acttccccaa ccccgaggag  3300
ttccagcctg agcggttctt ccccgagaat gcacaagggc gccatccata tgcctacgtg  3360
cccttctctg ctggccccag gaactgtata ggtcaaaagt ttgctgtgat ggaagaaaag  3420
accattcttt cgtgcatcct gaggcacttt tggatagaat ccaaccagaa aagagaagag  3480
cttggtctag aaggacagtt gattcttcgt ccaagtaatg gcatctggat caagttgaag  3540
aggagaaatg cagatgaacg ctaaagatct gcctcgactg tgccttctag ttgccagcca  3600
tctgttgttt gcccctcccc cgtgccttcc ttgaccctgg aaggtgccac tcccactgtc  3660
ctttcctaat aaaatgagga aattgcatcg cattgtctga gtaggtgtca ttctattctg  3720
gggggtgggg tggggcagga cagcaagggg gaggattggg aagacaatag caggcatgct  3780
```

-continued

```
ggggatgcgg tgggctctat ggatccccta actacaagga acccctagtg atggagttgg  3840
ccactccctc tctgcgcgct cgctcgctca ctgaggccgg gcgaccaaag gtcgcccgac  3900
gcccgggctt tgcccgggcg gcctcagtga gcgagcgagc gcgcagagag ggagtggcca  3960
a                                                                  3961

SEQ ID NO: 17          moltype =   length =
SEQUENCE: 17
000

SEQ ID NO: 18          moltype = DNA  length = 23
FEATURE                Location/Qualifiers
source                 1..23
                       mol_type = other DNA
                       organism = synthetic construct
SEQUENCE: 18
agtatgtccg tgcagtttat agg                                          23

SEQ ID NO: 19          moltype = DNA  length = 23
FEATURE                Location/Qualifiers
source                 1..23
                       mol_type = other DNA
                       organism = synthetic construct
SEQUENCE: 19
catacaggtc atcgctgaac ggg                                          23

SEQ ID NO: 20          moltype = DNA  length = 23
FEATURE                Location/Qualifiers
source                 1..23
                       mol_type = other DNA
                       organism = synthetic construct
SEQUENCE: 20
tcatacaggt catcgctgaa cgg                                          23

SEQ ID NO: 21          moltype = DNA  length = 23
FEATURE                Location/Qualifiers
source                 1..23
                       mol_type = other DNA
                       organism = synthetic construct
SEQUENCE: 21
gattatcatt caaatcatac agg                                          23

SEQ ID NO: 22          moltype = DNA  length = 20
FEATURE                Location/Qualifiers
source                 1..20
                       mol_type = other DNA
                       organism = synthetic construct
SEQUENCE: 22
gaaatcacac tccaccggga                                              20

SEQ ID NO: 23          moltype = DNA  length = 24
FEATURE                Location/Qualifiers
source                 1..24
                       mol_type = other DNA
                       organism = synthetic construct
SEQUENCE: 23
acctttactg cttaaacaca tgct                                         24

SEQ ID NO: 24          moltype = DNA  length = 20
FEATURE                Location/Qualifiers
source                 1..20
                       mol_type = other DNA
                       organism = synthetic construct
SEQUENCE: 24
caggcagcag aaatcgcaag                                              20

SEQ ID NO: 25          moltype = DNA  length = 20
FEATURE                Location/Qualifiers
source                 1..20
                       mol_type = other DNA
                       organism = synthetic construct
SEQUENCE: 25
agcctgttcc cttcgtcatc                                              20

SEQ ID NO: 26          moltype = DNA  length = 102
FEATURE                Location/Qualifiers
source                 1..102
                       mol_type = other DNA
                       organism = synthetic construct
SEQUENCE: 26
```

-continued

```
taactagggt gcatccaagt ccaaacagaa gcatgtgatt atcattcaaa gcgaacgggc  60
caatgaaatg aacgccaatg aagactgtag aggtgatggc ag                     102

SEQ ID NO: 27          moltype = AA  length = 525
FEATURE                Location/Qualifiers
source                 1..525
                       mol_type = protein
                       organism = synthetic construct
SEQUENCE: 27
MAGLWLGLVW QKLLLWGAAS ALSLAGASLV LSLLQRVASY ARKWQQMRPI PTVARAYPLV  60
GHALLMKPDG REFFQQIIEY TEEYRHMPLL KLWVGPVPMV ALYNAENVEV ILTSSKQIDK  120
SSMYKFLEPW LGLGLLTSTG NKWRSRRKML TPTFHFTILE DFLDIMNEQA NILVKKLEKH  180
INQEAFNCFF YITLCALDII CETAMGKNIG AQSNDDSEYV RAVYRMSEMI FRRIKMPWLW  240
LDLWYLMFKE GWEHKKSLQI LHTFTNSVIA ERANEMNANE DCRGDGRGSA PSKNKRRAFL  300
DLLLSVTDDE GNRLSHEDIR EEVDTFMFEG HDTTAAAINW SLYLLGSNPE VQKKVDHELD  360
DVFGKSDRPA TVEDLKKLRY LECVIKETLR LFPSVPLFAR SVSEDCEVAG YRVLKGTEAV  420
IIPYALHRDP RYFPNPEEFQ PERFFPENAQ GRHPYAYVPF SAGPRNCIGQ KFAVMEEKTI  480
LSCILRHFWI ESNQKREELG LEGQLILRPS NGIWIKLKRR NADER                  525

SEQ ID NO: 28          moltype = DNA  length = 1575
FEATURE                Location/Qualifiers
source                 1..1575
                       mol_type = other DNA
                       organism = synthetic construct
SEQUENCE: 28
atggcggggc tctggctggg gctcgtgtgg cagaagctgc tgctgtgggg cgcggcgagt  60
gccctttccc tggccggcgc cagtctggtc ctgagcctgc tgcagagggt ggcgagctac  120
gcgcggaaat ggcagcagat gcggcccatc cccacggtgg cccgcgccta cccactggtg  180
ggccacgcgc tgctgatgaa gccggacggg cgagaatttt ttcagcagat cattgagtac  240
acagaggaat accgccacat gccgctgctg aagctctggg tcgggccagt gcccatggtg  300
gccctttata atgcagaaaa tgtggaggta attttaacta gttcaaagca aattgacaaa  360
tcctctatgt acaagttttt agaaccatgg cttggcctag gacttcttac aagtactgga  420
aacaaatggc gctccaggag aaagatgtta acacccactt tccattttac cattctggaa  480
gatttcttag atatcatgaa tgaacaagca aatatattgg ttaagaaact tgaaaaacac  540
attaaccaag aagcatttaa ctgctttttt tacatcactc tttgtgcctt agatatcatc  600
tgtgaaacag ctatggggaa gaatattggt gctcaaagta atgatgattc cgagtatgtc  660
cgtgcagttt atagaatgag tgagatgata tttcgaagaa taaagatgcc ctggctttgg  720
cttgatctct ggtaccttat gtttaaagaa ggatgggaac acaaaaagag ccttcagatc  780
ctacatactt ttaccaacag tgtcatcgct gaacgggcca atgaaatgaa cgccaatgaa  840
gactgtagag gtgatggcag gggctctgcc ccctccaaaa ataaacgcag ggcctttctt  900
gacttgcttt taagtgtgac tgatgacgaa gggaacaggc taagtcatga agatattcga  960
gaagaagttg acaccttcat gtttgagggg cacgatacaa ctgcagctgc aataaactgg  1020
tccttatacc tgttgggttc taacccagaa gtccagaaaa aagtggatca tgaattggat  1080
gacgtgtttg ggaagtctga ccgtcccgct acagtagaag acctgaagaa acttcggtat  1140
ctggaatgtg ttattaagga gacccttcgc ctttttcctt ctgttccttt atttgcccgt  1200
agtgttagtg aagattgtga agtggcaggt tacagagttc taaaaggcac tgaagccgtc  1260
atcattccct atgcattgca cagagatccg agatacttcc ccaaccccga ggagttccag  1320
cctgagcggt tcttccccga gaatgcacaa gggcgccatc catatgccta cgtgcccttc  1380
tctgctggcc ccaggaactg tataggtcaa aagtttgctg tgatggaaga aaagaccatt  1440
ctttcgtgca tcctgaggca cttttggata gaatccaacc agaaaagaga agagcttggt  1500
ctagaaggac agttgattct tcgtccaagt aatggcatct ggatcaagtt gaagaggaga  1560
aatgcagatg aacgc                                                   1575
```